United States Patent
Onuoha et al.

(10) Patent No.: US 12,241,124 B2
(45) Date of Patent: Mar. 4, 2025

(54) MOLECULAR ASSESSMENT OF TRBC USAGE

(71) Applicant: AUTOLUS LIMITED, London (GB)

(72) Inventors: Shimobi Onuoha, London (GB); Meggan Czapiga, London (GB); Biao Ma, London (GB)

(73) Assignee: AUTOLUS LIMITED, London (GB)

( * ) Notice: Subject to any disclaimer, the term of this patent is extended or adjusted under 35 U.S.C. 154(b) by 692 days.

(21) Appl. No.: 17/264,217

(22) PCT Filed: Jul. 18, 2019

(86) PCT No.: PCT/GB2019/052011
§ 371 (c)(1),
(2) Date: Jan. 28, 2021

(87) PCT Pub. No.: WO2020/025928
PCT Pub. Date: Feb. 6, 2020

(65) Prior Publication Data
US 2022/0010377 A1 Jan. 13, 2022

(30) Foreign Application Priority Data
Aug. 3, 2018 (GB) ..................................... 1812650

(51) Int. Cl.
*C12Q 1/6881* (2018.01)
*C12Q 1/6886* (2018.01)

(52) U.S. Cl.
CPC ......... *C12Q 1/6881* (2013.01); *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2017/0066827 A1 | 3/2017 | Pule et al. |
| 2017/0334998 A1 | 11/2017 | Pule et al. |
| 2018/0201991 A1 | 7/2018 | Zhang et al. |
| 2019/0209612 A1 | 7/2019 | Pule et al. |
| 2020/0140549 A1 | 5/2020 | Cordoba et al. |
| 2020/0200756 A1 | 6/2020 | Pule et al. |

FOREIGN PATENT DOCUMENTS

| | | |
|---|---|---|
| AU | 2015225944 A1 | 9/2016 |
| CN | 102443624 A | 5/2012 |
| CN | 102443624 B | 12/2014 |
| CN | 103205420 B | 4/2015 |
| EP | 3211003 A1 | 8/2017 |
| WO | WO-2015/132598 A1 | 9/2015 |
| WO | WO-2016/051205 A1 | 4/2016 |
| WO | WO-2018/224844 A1 | 12/2018 |
| WO | WO-2020/084290 A1 | 4/2020 |
| WO | WO-2020/089644 A1 | 5/2020 |

OTHER PUBLICATIONS

Raeburn, L.A. Characterization of TCR ß sequence diversity in colorectal carcinoma. Thesis Dissertation. Published 2012. Simon Fraser University, available via URL: <summit.sfu.ca/_flysystem/fedora/sfu_migrate/12419/etd7386_LRaeburn.pdf>, 116 pages (Year: 2012).*
Benson et al., Nucleic Acids Res. 45(D1):D37-D42 (2017).
Bolotin et al. "MiXCR: software for comprehensive adaptive immunity profiling," Nature Methods 12(5):380-381 (2015).
International Search Report and Written Opinion from International Application No. PCT/GB2019/052011 dated Oct. 17, 2019.
Lefranc et al,. "IMGT®, the international ImMunoGeneTics information system® 25 years on," Nucleic Acids Res. 43:D413-22 (2015).
Lefranc et al., "IMGT, the international ImMunoGene Tics database," Nucleic Acids Research 31(1):307-310 (2003).
Lefranc et al., "Immunoglobulin and T cell receptor genes: IMGT® and the birth and rise of immunoinformatics," Front Immunol. 22(5), 22 pages (2014).
Lefranc, "IMGT, the International ImMunoGeneTics Information System" Cold Spring Harb Protoc. 2011(6):595-603 (2011).
Lethe et al., "A new transcript in the TCRB locus unveils the human ortholog of the mouse pre-Db1 promoter," Immunity, Inflammation and Disease 5(3):346-354 (2017).
Maciocia et al., "Targeting the T cell receptor ß-chain constant region for immunotherapy of T cell malignancies," Nature Medicine 23(12):1416-1423 (2017).
van Dongen et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia 17:2257-2317 (2003).
Tokudome, "MacBook Pro (13-inch, Mid 2012) Memory Replacement CPU, Memory and HD", Kurachic Real Estate [online], Sep. 29, 2017, pp. 1-9.

* cited by examiner

*Primary Examiner* — Carla J Myers
(74) *Attorney, Agent, or Firm* — MARSHALL, GERSTEIN & BORUN LLP

(57) ABSTRACT

The invention relates to a method of determining the T cell receptor β chain (TRBC) gene type of a cell, the method comprising (a) determining the J gene type expressed in said cell, and (b) inferring from (a) the TRBC gene type expressed in said cell. The invention further relates to use of a CAR T cell targeted to a T cell receptor β chain (TRBC) type 1, or a CAR T cell targeted to a T cell receptor β chain (TRBC) type 2. The invention further relates to a method of medical treatment, and to nucleic acid probes.

1 Claim, 6 Drawing Sheets

Specification includes a Sequence Listing.

| Input | Vname | 3' V-REGION | N1 | D-REGION | N2 | 5' J-REGION | Jname | Dname | Vmut | Dmut | Jmut | Ngc |
|---|---|---|---|---|---|---|---|---|---|---|---|---|
| SEQ ID No. 37 38675309_B97#1_TRBC2 | Homsap TRBV29-1*01 | tgcagcg........ | ccaaa | gggac........ | cct | ...ctacgagcagtacttc | Homsap TRBJ2-7*01 | Homsap TRBD1*01 | 0 | 0 | 0 | 4/8 |

FIG. 4

FIGURE 5 a) V-region translation and alignment

```
                         <-------------------------------- FR1 - IMGT ---------------------------><-- CDR1 - IMGT -->
       1               5               10              15              20              25              30               35
       S   A   V   I   S   Q   K   P   S   R   D   I   C   Q   R   G   T   S   L   T   I   Q   C   Q   V   D   S   Q   V                       T   M      SEQ ID No. 33
1) agt gct gtc atc tct caa aag cca agc agg gat atc tgt caa cgt gga acc tcc ctg acg atc cag tgt caa gtc gat agc caa gtc ... ... ... ...              SEQ ID No. 32
2) ...  ... ... ... ... ... ... ... ... ... ... ... ... ... ... ... ... ... ... ... ... ... ... ... ... ... ... ... ...              acc at <-------- CDR2 - IMGT -------->                              <-------------- FR3 - IMGT
       40              45              50              55              60              65              70               75
       M   F   W   Y   R   Q   Q   P   G   Q   S   L   T   L   I   A   T   A   N   Q   G   S   E   A   T   Y   E   S   G   F   V   I   D   K
1) g atg ttc tgg tac cgt cag caa cct gga cag agc ctg aca ctg atc gca act gca aat cag ggc tct gag gcc aca tat gag agt gga ttt gtc att gac aag
2) ...   ... ... ... ... ... ... ... ... ... ... ... ... ... ... ... ... ... ... ... ... ... ... ... ... ... ... ... ... ... ... ... ... ...

---------------------------->                                              <------- CDR3 - IMGT
       80              85              90              95              100             104
       F   P   I   S   R   P   N   L   T   F   S   T   L   T   V   S   N   M   S   P   E   D   S   S   I   Y   L   C   S   V   E         T   L   Y   E   Q   SEQ ID No. 34
1) ttt ccc atc agc cgc cca ... aac cta aca ttc tca act ctg act gtg agc aac atg agc cct gaa gac agc agc ata tat ctc tgc agc gtt gaa ga          SEQ ID No. 35
2) ...  ... ... ... ... ... ... ... ... ... ... ... ... ... ... ... ... ... ... ... ... ... ... ... ... ... ... ... ... ...       ...cc a---gg acc ctc tac gag ca
                                                                                                                                              A   K   G   T   L   Y   E   Q Y   F   G   P   G   T   R   L   T   V   T
1) 
2) g tac ttc ggg ccg ggc acc agg ctc acg gtc aca g
```

KEY:
1) L36092 Homsap TRBV29-1*01 F Folch, G. and Lefranc, M.-P., Exp. Clin. Immunogenet., 17, 42-54 (2000) (L36092 – GenBank germline beta T-cell receptor locus)
2) 38675309_B97#1_TRBC2 (SEQ ID NQ: 31)

FIGURE 5 (cont.)

b) Analysis of the junction region (IMGT)

| Input | V name | 3'V-REGION | N1 | D-REGION | N2 | J-REGION | D name | J name |
|---|---|---|---|---|---|---|---|---|
| 38675309_B97#1_TRBC2 | Homsap TRBV29-1*01 | tgcagcg | ccaaa | gggac | cct | ctacgagcagtacttcgggccgggcaccaggctcacggtcaca | Homsap TRBD1*01 | Homsap TRBJ2-7*01 |
| | | | | | | | | SEQ ID No. 36 |

```
              FR1-IMGT            CDR1-IMGT            FR2-IMGT          CDR2-IMGT                    FR3-IMGT
              (1-26)              (27-38)              (39-55)           (56-65)                      (66-104)
      1       10         20             30         40         50         60         70         80         90        100
      |........|.........|.........|.........|.........|.........|.........|.........|.........|.........|
1) ...SAVISQKPSRDICQRGTSLTIQCQVD SQV........TM MFWYRQQPGQSLTLIAT ANQG...SEA TYESGFVIDKFPISRP.NLTFSTLTVSNMSPEDSSIYLC SVE SEQ ID No. 33
2)                                                                                                                  -AKGTLYEQYFGPGTRLTVT
SEQ ID NO. 34
```

KEY:
1) L36092 Homsap TRBV29-1*01 F (Folch, G. and Lefranc, M.-P., Exp. Clin. Immunogenet., 17, 42-54 (2000)) (L36092 - GenBank germline beta T-cell receptor locus)
2) 3675309_B97#1_TRBC2 (SEQ ID NO: 31)

MOLECULAR ASSESSMENT OF TRBC USAGE

CROSS-REFERENCE TO RELATED APPLICATIONS

This application is a U.S. National Phase of International Application No. PCT/GB2019/052011, filed Jul. 18, 2019, which claims priority to Great Britain Application No. 1812650.8, filed Aug. 3, 2018.

INCORPORATION BY REFERENCE OF THE SEQUENCE LISTING

This application contains, as a separate part of disclosure, a Sequence Listing in computer-readable form (Filename: 55130_SubSeqListing.txt; 8,698 bytes—Text file dated May 8, 2024) which is incorporated by reference herein in its entirety.

FIELD OF THE INVENTION

The invention is in the field of molecular assessment of T cell receptor β chain (TRBC) usage such as in peripheral T-cell lymphomas (PTCL), in particular determining the constant region gene type expressed in particular cell(s) such as PTCL.

BACKGROUND TO THE INVENTION

Peripheral T-cell lymphomas (PTCLs) represent 10% to 15% of non-Hodgkin's lymphomas and are composed of 23 different entities. Standard of care in this subset of diseases is variable and 65% of patients are refractory or relapse after standard therapy. A paucity of specific targets for PTCLs has hampered the development of targeted immunotherapies for these diseases.

The αβ TCR is a pan-T cell antigen. Apart from its expression on normal T cells, it is a highly promising target for treatment of PTCL.

Thus, one approach to treatment of T-cell leukaemias and/or lymphomas is to target the T-cell receptor as an antigen. This approach can lead to efficient destruction of cells bearing that antigen—an approach which has been very effective for B-cell malignancies. However, in contrast with B-cell ablation, removal of the T-cell population from a patient is not well tolerated. The severe toxicity associated with ablation of the T-cell compartment adds risk to targeting antigens that are expressed on healthy T-cells. This is extremely toxic leaving the patient dangerously exposed to infection.

A feature of the TCR β-chain recombination is that there are two genes associated with the β-chain constant region: TRBC1 and TRBC2. Each T cell (and thus each T cell cancer) irreversibly selects either TRBC1 or TRBC2 to incorporate into TCRs.

Approximately 35% of normal and virus-specific T cells express TRBC1, and 65% express TRBC2. Targeting tumours that express TRBC1 should deplete the tumour cells while the remaining T cells are left to expand, fill the T cell compartment and fight infection.

CAR T cells that target TRBC1, but not TRBC2, to treat mature T cell cancers have been described. Key to the success of this strategy is the selection of patients with lymphomas that express the correct TCR beta constant region.

Determining the TRBC1 or TRBC2 type of T-cells (T-cell cancers) is a problem in the art.

Strategies have been described that cover the general diagnosis of T cell lymphoma patients whereby the percentage of total T-cells in a sample of tumour isolated from the subject is ascertained to be TRBC1 or TRBC2 positive. Targeted killing of TRBC1+ T-cells using anti-TRBC1 chimeric antigen receptor (CAR) T cells is described (Maciocia et al 2017 Nature Medicine volume 23, pages 1416-1423). Cells expressing TRBC1/TRBC2 were distinguished using the JOVI-1 mAb, which is specific for TRBC1-expressing cells. This is laborious, and IHC methods can be subjective, which are drawbacks with this approach.

WO2016051205A1 discloses a method of investigating the monotypia of a population of T-cells comprising detecting expression of the T cell receptor beta chain constant region TRBC1 and TRBC2, and/or the T cell receptor gamma chain constant region TRGC1 and TRGC, in a population of T-cells. The techniques described are focussed on IHC and/or RNA based direct detection of constant regions. These methods can be unreliable (e.g. IHC) and/or require RNA preservation/extraction (e.g. direct detection), both of which are drawbacks with these methods.

WO2015/132598 (corresponding to AU2015225944) describes TRBC1 and TRBC2-specific chimeric antigen receptors (CARs) for use in the treatment of T-cell malignancies. However, accurately determining the TRBC1/TRBC2 type of the malignancy remains a problem in the art.

The present invention seeks to overcome problem(s) associated with the prior art.

SUMMARY OF THE INVENTION

Targeting only tumours that express TRBC1 or tumours that express TRBC2 should deplete the tumour cells while the remaining T cells are left to expand, fill the T cell compartment and fight infection.

A method is described herein which allows a molecular diagnosis of a patient tumour to determine if the tumour is comprised of TRBC1 or TRBC2 expressing cells. The method offers significant advantages over other methods in that it allows the diagnosis to be made on any patient sample from which nucleic acid, preferably genomic DNA, can be obtained.

Thus, the invention provides a diagnostic test which enables TRBC typing of a sample from a patient. In this way, an appropriate therapy can be selected for the patient (i.e. to target TRBC1 expressing cells, or to target TRBC2 expressing cells).

The approach taught by the invention advantageously uses genomic DNA analysis to determine the TRBC type of the cells in the sample. The inventors have discovered a surprisingly close genetic linkage of the J region (joining region) to the C region (constant region) of the TCR gene. The inventors had the insight that the TRBC type of the cell could be read out by studying the J region, making use of the newly discovered linkage of the J region to the C region, and inferring the TRBC type of the C region of interest.

It is surprising that this approach is successful given that the C region and the J region are separated by a very large amount of intervening nucleic acid. This amount of genetic distance would normally lead to a far looser linkage between the J and C regions. For these reasons, it is very surprising that such a reliable and tight linkage between J and C regions is observed, making the diagnostic methods of the invention possible.

It is a further advantage of the invention that this accurate genetic approach is better and more accurate than any "by eye" immunohistochemistry (IHC) based method.

Prior art approaches have taught the use of antibodies for determining TRBC type of a sample. However, antibody based approaches require subjective judgements and/or human intervention in order to assess their output. It is an advantage of the invention that a binary answer (TRBC1 or TRBC 2) is provided.

The extremely high reliability and extremely low error rate (e.g. recombination rate) between determining the J region gene and inferring the C region gene which are present is very surprising. Even if a skilled person had contemplated that the two genes might be linked, they would never have predicted that they would be linked so tightly as to provide reliable diagnostic information as taught by the invention.

It is well known in the art that many antibodies do not bind their epitopes in fixed tissue, but rather only bind them in fresh or frozen tissue. As is well known in the art, fixing of tissue can affect the protein structure and therefore it is very common for antibodies to recognise epitopes which are not present/not available in one or other sample type. It is an advantage of the invention that by using genetic methods, the test works equally well on fixed or fresh or frozen tissues. Thus the invention is widely applicable to any sample type, which overcomes limitations of prior art approaches such as IHC analysis.

Thus in one aspect, the invention relates to a method of determining the T cell receptor β chain (TRBC) gene type of a cell, the method comprising
  (a) determining the J gene type expressed in said cell, and
  (b) inferring from (a) the TRBC gene type expressed in said cell.

'J gene' has its normal meaning in the art. Suitably 'J gene' refers to the junctional or joining segment (J region) of the T cell receptor gene.

Suitably the term 'V region' has its normal meaning in the art i.e. the variable region or variable section (V region) of the T cell receptor gene.

Suitably the term 'C region' has its normal meaning in the art i.e. the constant region or constant section (C region) of the T cell receptor gene.

Suitably the term 'D region' has its normal meaning in the art i.e. the diversity region or diversity section (D region) of the T cell receptor gene.

In the event that further guidance is needed, an annotated reference sequence is provided below.

Suitably step (a) comprises:
  (i) extracting nucleic acid from said cell;
  (ii) determining the nucleotide sequence of at least a segment of said J gene from said nucleic acid; and
  (iii) comparing the nucleotide sequence determined in (ii) to one or more J gene reference nucleotide sequence(s), and
  (iv) identifying the J gene type from sequence identity of the nucleotide sequence of the segment of said J gene of (ii) to the J gene reference nucleotide sequence(s) of (iii).

Suitably said J gene reference nucleotide sequence(s) are as in Table 1.

When considering sequence identity of the nucleotide sequence of the segment of said J gene of (ii) to the J gene reference nucleotide sequence(s) of (iii), a sufficient level of sequence identity to identify the J gene reference nucleotide sequence (i.e. identify the J gene type) with appropriate scientific/statistical confidence is required. Suitably a 100% sequence identity match to the J gene reference nucleotide sequence is required. Suitably the sequence identity is assessed across the whole length of the J gene reference nucleotide sequence. Suitably the query sequence and the J gene reference nucleotide sequence may need to be aligned before the sequence identity determination is made. Alignment of sequences may be done by eye or may be done using a known sequence alignment tool such as discussed below.

Suitably said nucleic acid comprises genomic DNA (gDNA).

Suitably said segment of said J gene comprises the whole J region of the T cell receptor gene.

Suitably said segment of said J gene is comprised by CDR3 of the T cell receptor gene.

Suitably said segment of said J gene is selected from the group consisting of:

| | |
|---|---|
| SEQ ID NO: 1 | tgaacactgaagctttctttggacaaggcaccagactcacagttgtag |
| SEQ ID NO: 2 | ctaactatggctacaccttcggttcggggaccaggttaaccgttgtag |
| SEQ ID NO: 3 | ctctggaaacaccatatattttggagagggaagttggctcactgttgtag |
| SEQ ID NO: 4 | caactaatgaaaaactgttttttggcagtggaacccagctctctgtcttgg |
| SEQ ID NO: 5 | tagcaatcagccccagcattttggtgatggactcgactctccatcctag |
| SEQ ID NO: 6 | ctcctataattcaccctccactttgggaatgggaccaggctcactgtgacag |
| SEQ ID NO: 7 | ctcctataattcaccctccactttgggaacgggaccaggctcactgtgacag |
| SEQ ID NO: 8 | ctcctacaatgagcagttcttcgggccagggacacggctcaccgtgctag |
| SEQ ID NO: 9 | cgaacaccggggagctgttttttggagaaggctctaggctgaccgtactgg |
| SEQ ID NO: 10 | ctgagaggcgctgctgggcgtctgggcggaggactcctggttctgg |
| SEQ ID NO: 11 | agcacagatacgcagtattttggcccaggcacccggctgacagtgctcg |
| SEQ ID NO:12 | agccaaaaacattcagtacttcggcgccgggacccggctctcagtgctgg |
| SEQ ID NO: 13 | accaagagacccagtacttcgggccaggcacgcggctcctggtgctcg |

-continued

| | |
|---|---|
| SEQ ID NO: 14 | ctctggggccaacgtc<br>ctgactttcggggccg<br>gcagcaggctgaccgt<br>gctgg |
| SEQ ID NO: 15 | ctcctacgagcagtac<br>ttcgggccgggcacca<br>ggctcacggtcacag |
| SEQ ID NO: 16 | ctcctacgagcagtac<br>gtcgggccgggcacca<br>ggctcacggtcacag |

Suitably step (ii) comprises:
(1) contacting said nucleic acid with reagents for amplification of at least a segment of said J gene;
(2) incubating to allow amplification;
(3) determining the nucleotide sequence of the amplified segment(s) of said J gene.

Suitably said reagents for amplification comprise at least one forward primer located in the V region of the T cell receptor gene and at least one reverse primer located in the J region of the T cell receptor gene, or wherein said reagents for amplification comprise at least one reverse primer located in the V region of the T cell receptor gene and at least one forward primer located in the J region of the T cell receptor gene.

Suitably said method further comprises:
(2a) carrying out electrophoresis of the amplified segment(s) of said J gene;
(2b) selecting dominant amplification product(s) from step (2a) for nucleotide sequencing.

Suitably step (a) comprises carrying out clonality determination or immunosequencing on said cell to provide nucleotide sequence information for said J gene, and determining the J gene type from said nucleotide sequence information.

Suitably determining the nucleotide sequence comprises NGS analysis.

In one embodiment suitably said cell is present within a population of cells, and wherein step (a) comprises:
(i) extracting nucleic acid from said population of cells;
(iia) determining the nucleotide sequence of at least a segment of said J gene from said nucleic acid to generate a population of nucleotide sequences;
(iib) selecting a nucleotide sequence from said population of nucleotide sequences;
(iii) comparing the nucleotide sequence selected in (iib) to one or more J gene reference nucleotide sequence(s), and
(iv) identifying the J gene type by sequence identity of the nucleotide sequence of the segment of said J gene of (iib) to the J gene reference nucleotide sequence(s) of (iii).

When the nucleotide sequence is determined by NGS and/or when the nucleotide sequence is determined for nucleic acid from a population of cells, it will be noted that a plurality of nucleotide sequences is generated during the sequence determination procedure. This is well known by the skilled operator. Thus the 'raw' nucleotide sequence data must be evaluated once determined by the NGS instrument. Inappropriate data is discarded.

For example, samples may be detected with 2 or more clonal rearrangements. Data from incomplete rearrangement(s) such as D/J rearrangements is suitably discarded. Focus is on the complete V/J rearrangements. Thus for samples showing 2 or more clonal rearrangements, rows of data are discarded when they relate to incomplete rearrangements such as D/J rearrangements or none-J rearrangements or other incomplete rearrangements. The V/J rearrangement sequence data are retained. Suitably the nucleotide sequence data is from a V/J rearranged nucleic acid.

For example, samples may not show clonality. Guidance for assessing clonality is well known in the art and is explained below and is presented in Table 3. For example, when the top % total reads less than 1.0%, data are considered non-clonal. Data which is non-clonal is suitably discarded. Focus is on data which is clonal. Suitably the nucleotide sequence data is from a clonal nucleic acid.

For example using the LymphoTrack NGS system, the minimum DNA input requirement is 50 ng per sample. According to the LymphoTrack NGS system IFU 280410, samples with less than 50 ng nucleic acid are considered as "Not evaluable". Data which is not evaluable is suitably discarded. Focus is on data which is evaluable. Suitably the nucleotide sequence data is from an evaluable sample. Suitably the nucleotide sequence data is from a sample comprising at least 50 ng nucleic acid.

Suitably said cell is from a subject having, or suspected of having, a peripheral T cell lymphoma (PTCL).

Suitably said cell is a peripheral T cell lymphoma (PTCL) cell.

In one aspect, the invention relates to a method of treating peripheral T cell lymphoma (PTCL) comprising
(a) determining the T cell receptor β chain (TRBC) type of a PTCL cell from said subject as described above; and
(b) administering to said subject a CAR T cell targeted to the T cell receptor β chain (TRBC) type determined in (a).

In one aspect, the invention relates to a CAR T cell targeted to a T cell receptor β chain (TRBC) type 1, or a CAR T cell targeted to a T cell receptor β chain (TRBC) type 2, for use in the treatment of peripheral T cell lymphoma (PTCL), wherein said treatment comprises the method of treating as described above.

In one aspect, the invention relates to a nucleic acid probe comprising nucleotide sequence, or consisting of nucleotide sequence, selected from the group consisting of:

| | |
|---|---|
| SEQ ID NO: 1 | tgaacactgaagcttt<br>ctttggacaaggcacc<br>agactcacagttgtag |
| SEQ ID NO: 2 | ctaactatggctacac<br>cttcggttcggggacc<br>aggttaaccgttgtag |
| SEQ ID NO: 3 | ctctggaaacaccata<br>tattttggagagggaa<br>gttggctcactgttgt<br>ag |
| SEQ ID NO: 4 | caactaatgaaaaact<br>gtttttggcagtgga<br>acccagctctctgtct<br>tgg |
| SEQ ID NO: 5 | tagcaatcagccccag<br>catttggtgatggga<br>ctcgactctccatcct<br>ag |
| SEQ ID NO: 6 | ctcctataattcaccc<br>ctccactttgggaatg<br>ggaccaggctcactgt<br>gacag |

-continued

| SEQ ID NO: 7 | ctcctataattcaccc
ctccactttgggaacg
ggaccaggctcactgt
gacag |
| SEQ ID NO: 8 | ctcctacaatgagcag
ttcttcgggccaggga
cacggctcaccgtgct
ag |
| SEQ ID NO: 9 | cgaacaccggggagct
gttttttggagaaggc
tctaggctgaccgtac
tgg |
| SEQ ID NO: 10 | ctgagaggcgctgctg
ggcgtctgggcggagg
actcctggttctgg |
| SEQ ID NO: 11 | agcacagatacgcagt
attttggcccaggcac
ccggctgacagtgctc
g |
| SEQ ID NO: 12 | agccaaaaacattcag
tacttcggcgccggga
cccggctctcagtgct
gg |
| SEQ ID NO: 13 | accaagagacccagta
cttcgggccaggcacg
cggctcctggtgctcg |
| SEQ ID NO: 14 | ctctggggccaacgtc
ctgactttcggggccg
gcagcaggctgaccgt
gctgg |
| SEQ ID NO: 15 | ctcctacgagcagtac
ttcgggccgggcacca
ggctcacggtcacag |
| SEQ ID NO: 16 | ctcctacgagcagtac
gtcgggccgggcacca
ggctcacggtcacag |

In one aspect, the invention relates to a nucleic acid array comprising at least two different nucleic acid probes as described above.

DETAILED DESCRIPTION

TCR diversity is generated by somatic recombination, which occurs when each TCR chain selects a variable (V), diversity (D), joining (J) and constant (C) region. TCR β-chain junctional regions segregate with constant domains. VDJ recombination occurs at the genomic DNA level, mRNA transcription splices out any intervening sequence and allows translation of the full length protein for the TCR Cβ chain. Due to the presence of a large intervening region between the TRBC1 and TRBC2 constant regions at the DNA level, it is disclosed herein that TCRs selecting TRBJ1-1 through TRBJ1-6 use TRBC1, and those selecting TRBJ2-1 through TRBJ2-7 use TRBC2. Thus we demonstrate that it is possible to infer the C region usage of a TCR by identifying the J-region used.

TCRs are not subject to somatic hypermutation when a given T cell is exposed to antigen. As such, the specificity of a given T cell clone remains static once rearrangement has occurred. TCR clonality testing is routinely used as a diagnostic tool for T cell lymphoproliferative disorders. Briefly, multiplexed primers are used to amplify the VDJ recombined variable regions, the presence of a dominant clone can be visualised through electrophoresis and sequencing of dominant PCR products can elucidate the tumour clonotype. Combination of TCR clonality with NGS sequencing enables measurement of millions of segments of the genome simultaneously and can overcome limitations associated with traditional sequencing such as the identification of a clone in the presence of large numbers of infiltrating T cells.

It is known that there two genes for the constant region of the T-cell receptor β chain (TRBC) —TRBC1 and TRBC2. These two genes are thought to have arisen by a genetic duplication, and are regarded as functionally equivalent. The two gene products differ by only four amino acids. Notwithstanding their similarities, the differences can be advantageously exploited since tumours are clonal. Therefore, each of the cells in a given malignancy will have the same TRBC gene as the original T-cell from which the tumour arose. Therefore, in a given patient all of the malignant cells will be either TRBC1 or TRBC2.

In any given individual, approximately 35% of normal T-cells express TRBC1, and the remaining 65% express TRBC2. This provides the opportunity to selectively target all TRBC1 expressing cells, whilst leaving all the TRBC2 expressing cells to survive (or vice versa). In this way, the malignancy can be targeted and whilst this will also target the population of the same TRBC type healthy T-cells in that patient, it will not target the remainder of the healthy T-cell population expressing the other TRBC type. Therefore, whichever TRBC type is targeted, the remaining part of the healthy T-cell population should be maintained within the patient, leaving them with an immune effector function whilst reducing or eliminating their malignancy. In order to implement this elegant therapy, it is vital to accurately and efficiently determine the TRBC gene which is expressed on any given patient's malignant cells. The present invention provides a solution to this problem.

We have demonstrated through NGS analysis of healthy human T cells, that in the overwhelming majority of cases TRBJ1 links to C1 and TRBJ2 links to C2. Diagnosis of TRBC1 or TRBC2 expression on patient tumours can thus be made through the analysis of J regions using clonality based assays.

Previous strategies used to identify TRBC1 or TRBC2 expressing tumours are predicated on the use of antibody staining methods which only work on flow cytometry assays or on fresh tissue. Because the described method interrogates DNA at the genomic level, fixed tissue may be used as the source material, which is an advantage of the invention.

The invention relates to molecular assessment of TRBC usage in T cell lymphomas. Suitably the molecular assessment is nucleic acid based assessment.

Suitably the cell is an in vitro cell.

The invention exploits the link between J1/C1 and J2/C2 using NGS analysis.

Cells/Sample

The invention may be applied to any cell expressing a T-cell receptor β chain. Suitably the cell is a mammalian cell, suitably the cell is a primate cell, suitably the cell is a human cell. Suitably the cell is, or is derived from, a T-cell.

A cell derived from a T-call includes a neoplastic cell such as a lymphoma cell and/or a tumour cell.

Suitably the cell may be a neoplastic cell. Suitably the cell may be a malignant cell. Suitably the cell may be a cancer cell. Suitably the cell may be a tumour cell.

Suitably the cell is comprised by, or is present in, a sample from a subject of interest. Suitably the sample may be a sample taken from the tumour or suspected tumour in the subject.

Suitably the sample may be a biopsy, such as a tumour biopsy.

Suitably the sample may be a blood sample. This is especially advantageous when using the invention to monitor minimal residual disease (MRD).

The sample may be a tonsil sample.

Suitably the method is an in vitro method. Suitably the sample is an in vitro sample. Suitably the sample has been previously collected from a subject. Suitably the method does not involve the collection of the sample from the human or animal body. Suitably the method is not practised on a human or animal body. Suitably the method does not require the presence of a human or animal body.

Computer Implementation

Suitably the method may be performed, at least in part, in silico.

In so far as the embodiments of the invention described above are implemented, at least in part, using software-controlled data processing apparatus, it will be appreciated that a computer program providing such software control and a storage medium by which such a computer program is stored are envisaged as aspects of the present invention.

Thus the invention provides a method of operating said data processing apparatus, the apparatus set up to execute the method, and/or the computer program itself. The invention also relates to physical media carrying the program such as a computer program product, such as a data carrier, storage medium, computer readable medium or signal carrying the program.

Clearly steps such as providing a sample would be embraced by such a computer program if a software controlled sample handling apparatus was employed. However, if such a step is performed manually at the choice of the operator, then the computer implemented method steps should be understood to comprise or consist of the data processing steps of the method.

In one aspect, the invention relates to a computer program product operable, when executed on a computer, to perform the method steps (a) and (b) as described above, suitably to perform the method steps (ii) to (iv) as described above, more suitably to perform the method steps (iia) to (iv) as described above, most suitably to perform the method steps (iii) and (iv) as described above.

In one aspect, the invention relates to a data carrier or storage medium carrying a computer program product as described above.

Population of Cells

The invention may be applied to a population of T-cells. For example, the invention may be applied to a population of T-cells, or cells derived from T-cells, in the sample of interest. In this scenario, it may be important to determine the TRBC type of a particular cell of interest within that population. Selection of the cell of interest within that population may be done physically, e.g. by using a sample from the tissue of interest such as from the tumour or suspected tumour of interest, or may be done computationally, for example by selecting a particular clone from within the population of nucleotide sequences determined from the population of cells subjected to the analysis. For example, it may be desirable to choose the sequence of the dominant clone i.e. the clone showing the greatest number of "reads" or nucleic acid molecules within the population analysed. Alternatively, the amplified nucleic acids may be separated for example by electrophoresis, and the dominant clone selected for sequencing at that stage. The particular mode used for picking the individual clone (and therefore the individual cell) within the analysis is a matter for operator choice. In this way, the invention may be advantageously applied to particular cell or cells within an analysis conducted on a population of cells.

Nucleic Acid

In a broad aspect, the nucleic acid may be any nucleic acid occurring in the cell.

Suitably the nucleic acid is DNA or RNA. Suitably the nucleic acid comprises, or consists of, DNA. Suitably the nucleic acid comprises, or consists of, genomic DNA (gDNA).

Nucleic acid such as DNA is suitably extracted from cell(s) in the sample using any technique known the skilled worker. Suitably nucleic acid is extracted using a standard commercially available DNA extraction kit. Most suitably nucleic acid is extracted using the GeneRead DNA FFPE Kit (Cat No./ID: 180134) from QIAGEN Ltd., Skelton House, Lloyd Street North, Manchester, M15 6SH, U.K.

Optionally the method of the invention comprises a further optional step of inferring the clonotype of the peripheral T-cell lymphoma (PTCL) from the information determined in steps (a) and (b).

Suitably the nucleic acid analysed in the invention is genomic DNA (gDNA). In one embodiment the invention might be practiced using RNA as the starting material/nucleic acid being analysed. However, RNA requires certain treatment to preserve it in the sample such as a biopsy. If this treatment is not carried out on the initial sample or biopsy, then it may necessitate re-biopsying the patient which is a second invasive procedure which is undesirable. Thus, it is an advantage of the invention that the nucleic acid analysed is suitably gDNA. gDNA is typically more stable than RNA.

When analysing minimal residual disease (MRD), RNA might be analysed. However, at the stage of monitoring MRD, typically the sequence of the tumour VDJ region has been determined. Thus, when following MRD in a patient, it would be typical to simply detect the known transcript in RNA extracted from a sample from that patient, for example using primers in the CDRs of that sequence. In this way, exquisite specificity is obtained from primers directed (for example) to a suitable part of the nucleic acid such as that encoding CDR3. Therefore, whilst the TRBC1/2 typing method of the invention can also be applied in monitoring MRD, this might advantageously be combined with an RNA based approach detecting the specific transcript of the tumour clone already determined during patient treatment.

CDRs (complementarity determining regions) are well known in the art, see for example (Kabat et al., Sequences of Proteins of Immunological Interest, 5th Ed. Public Health Service, National Institutes of Health, Bethesda, Md. (1991)) and numerous subsequent publications describing and defining these regions.

T Cell Receptor β Chain (TRBC) Gene—Reference Sequence

Suitably all sequences herein are discussed with reference to human TRBC.

It may be helpful to refer to the GenBank sequence of the wild-type human gene.

The structure of the overall locus/composite gene including the V-D-J-C regions is known in the art, including the sequences of C1 type, C2 type, J1 type and J2 type. There are at least 7 J1 variants and 9 J2 variants. If further guidance is required, we refer to Table 1.

GenBank is a sequence database as described in Benson, D. et al, Nucleic Acids Res. 45 (D1): D37-D42 (2017). In more detail, GenBank is as administered by the National Center for Biotechnology Information, National Library of Medicine, 38A, 8N805, 8600 Rockville Pike, Bethesda, MD 20894, USA. Suitably the current version of sequence database(s) are relied upon. Alternatively, the release in force at the date of filing is relied upon. For the avoidance of doubt, NCBI-GenBank Release 225.0 (15 Apr. 2018) is relied upon.

In case any further guidance is required, we refer to the following reference sequence (SEQ ID NO: 31): >38675309_B97 #1_TRBC2

```
CGACGTGGATTATCCATGAACGCAAAGCAGTGGTATCAACGCAGAGTACGCGGGagggga gaggccatcacttgaagatgctgagtcttctgctccttctcctgggactaggctctgtgt tgagtgctgtcatctctcaaaagccaagcagggatatctgtcaacgtggaacctccctga cgatccagtgtcaagtcgatagccaagtcaccatgatgttctggtaccgtcagcaacctg gacagagcctgacactgatcgcaactgcaaatcagggctctgaggccacatatgagagtg gatttgtcattgacaagtttcccatcagccgcccaaacctaacattctcaactctgactg tgagcaacatgagccctgaagacagcagcatatatctctgcagcgccaaagggaccctct acgagcagtacttcgggccgggcaccaggctcacggtcacagaggacctgaaaaacgtgt tcccacccgaggtcgctgtgtttgagccatcagaagcagagatctcccacacccaaagg ccacactg
```

Bold = Variable/V
Italics = Diversity/D
Underlined = Junctional (Joining/J)
Boxed = Constant/C
CAPITALS = matches the template-switch primer for 5'RACE
dashed boxed = 5' untranslated region
double boxed = leader sequence Suitably a joining or J region comprises, or more suitably consists of, sequence corresponding to the sequence underlined above. More suitably a joining or J region comprises, or more suitably consists of, the sequence underlined above.

In more detail, SEQ ID NO: 31 is a reference sequence for a re-arranged beta chain. This is an example from an NGS library sequenced by the inventors.

When particular nucleotides are referred to herein using numeric addresses, the numbering is taken with reference to the wild type TRBC nucleotide sequence as shown above (e.g. SEQ ID NO: 31). This sequence is to be used as is well understood in the art to locate the feature/residue of interest. This is not always a strict counting exercise-attention must be paid to the context. For example, if the sequence of interest is of a slightly different length, then location of the correct nucleotide in that sequence may require the sequences to be aligned and the equivalent or corresponding nucleotide picked. This is well within the ambit of the skilled reader.

Determining V/D/J/C Regions

Clearly it is expected that there will be sequence variation between individual patients. This is true for all mammalian genes due to individual genetic variability/allelic differences. However, as is well known, this is especially the case for hypervariable regions such as the TRBC gene regions which are the subject of the present invention. Therefore, in examining a nucleotide or amino acid sequence and deciding whether it is a V/J/D/C region, or none of the above, standard approaches such as bioinformatic approaches using software (for example IMGT™ software) may be employed.

IMGT™, the international ImMunoGeneTics information System™ http://www.imgt.org, is the global reference in immunogenetics and immunoinformatics, created in 1989 by Marie-Paule Lefranc (Université de Montpellier and CNRS). IMGT™ is a high-quality integrated knowledge resource specialised in the immunoglobulins (IG) or antibodies, T cell receptors (TR), major histocompatibility (MH) of human and other vertebrate species, and in the immunoglobulin superfamily (IgSF), MH superfamily (MhSF) and related proteins of the immune system (RPI) of vertebrates and invertebrates. IMGT™ provides a common access to sequence, genome and structure Immunogenetics data, based on the concepts of IMGT-ONTOLOGY and on the IMGT Scientific chart rules.

In the event that any further information is required, we refer to Lefranc M-P, Giudicelli V, Duroux P, Jabado-Michaloud J, Folch G, Aouinti S, Carillon E, Duvergey H, Houles A, Paysan-Lafosse T, Hadi-Saljoqi S, Sasorith S, Lefranc G, Kossida S. Nucleic Acids Res. 2015 January; 43 (Database issue): D413-22. "IMGT™, the international ImMunoGeneTics information System™ 25 years on.", Lefranc, M.-P., Front Immunol. 2014 Feb. 5; 5:22 "Immunoglobulin (IG) and T cell receptor genes (TR): IMGT™ and the birth and rise of immunoinformatics.". Use of the IMGT™ tools is well within the ability of the skilled worker, and full details have been published and regularly updated since 1989, for example Lefranc, M.-P., Cold Spring Harb Protoc. 2011 Jun. 1; 2011 (6) "IMGT™, the International ImMunoGeneTics Information System".

In the unlikely event that further guidance is needed, in order to identify the J region a person skilled in the art can align sequences with a known alignment tool such as IMGT/V-quest (Nucleic Acids Res., 31, 307-310 (2003)).

IMGT/V-QUEST is a sequence alignment software for the immunoglobulin (IG) and T cell receptor (TR) nucleotide sequences of the variable regions and domains. The IMGT output comprises nucleotide and amino acid sequences of the junction.

Analysis of VDJ rearrangement is illustrated in FIG. 5A-B.

IMGT was to analyse the sequence of the B97 #1 TCR (SEQ ID no 31).

Other bioinformatics tools can be used to perform similar analysis to identify V/D/J/C regions, one example of which is the MiXCR software (Bolotin et al 2015 Nature Methods Vol 12 No. 5 pages 380-381). Bolotin et al discloses software providing a universal framework that processes big immunome data from raw sequences to quantitated clonotypes which is useful in identification of V/D/J/C regions in sequences of the present disclosure. Bolotin et al 2015 is specifically incorporated by reference solely for the teaching of such methods of analysis and no other purpose. Software is available for example from MiLaboratory LLC, 534 S. Andres Dr., Solana Beach, CA 92075, USA.

Mutating has it normal meaning in the art and may refer to the substitution or truncation or deletion or addition of one or more nucleotides, motifs or domains.

Sample

Suitably the sample may comprise a biopsy. Suitably the sample may comprise a tumour biopsy, or a biopsy from a suspected tumour. Suitably the sample may comprise blood. Suitably the sample may comprise a T-cell rich biopsy such a lymph node biopsy or a spleen biopsy.

It should be noted that the invention has been demonstrated using different sample types, such as tonsil biopsy. Tonsil is a T-cell rich tissue. This is very helpful in demonstrating the effectiveness of the invention, but is not necessarily an exemplary sample type when applying the invention to a patient. Thus, although tonsil is a suitable sample for the invention, more suitably the sample comprises a tumour biopsy, a suspected tumour biopsy, a lymph node biopsy, a spleen biopsy, or blood: more suitably the sample comprises a tumour biopsy or blood.

When the sample is from a tumour, suitably the sample may be from any tumour type or subtype. Suitably the sample may be from any tumour type or subtype mentioned in the examples section below.

Read Out

In principle, any way of reading out the sequence information from the nucleic acid(s), such as PCR amplified nucleic acid(s), derived from the sample may be used. For example, the PCR products may be separated by size such as using gel electrophoresis, and the dominant product may be excised and sequenced. Alternatively, TRBC1/2 specific primers may be used, for example in a secondary PCR after the initial amplification step, thereby giving an indication whether the sample is TRBC1 or TRBC2. However, more suitably, PCR primers specific to the J region being analysed might be used in a PCR reaction following the initial amplification, thereby indicating which J region is present in the sample and thereby allowing the identity of the C region to be inferred according to the methods of the invention.

In principle, hybridisation of nucleic acid probes might be used to detect the identity of the J region of the PCR product, or the amplified nucleic acid(s) could be applied to an array bearing one or more probe nucleic acids, hybridisation could be allowed to occur, and the identity of the J region in the PCR product could be read out by analysing the hybridisation pattern to those probe sequences.

C/J Regions

A key part of the invention is to exploit the tight linkage of C to J, and thereby infer the TRBC1/2 status indirectly from the J type.

An advantage of the invention is that it enables the detection (e.g. via nucleic acid amplification) from gDNA which is preserved in a greater number of tissue types and storage conditions than other nucleic acids such as RNA. Thus suitably the nucleic acid interrogated by the invention is gDNA (i.e. the starting material or the material analysed is suitably gDNA).

This is an advantage because when the source material is DNA such as gDNA, the intron between J and C regions is too large to cover using current sequencing technologies. Therefore the invention delivers a technical advantage by inferring the C region type from an analysis of the J region.

PCR Strategy

To determine the J type of a cell, typically nucleotide sequence information of the J region of that cell is required. Currently direct sequencing of gDNA from cells is not practical. Therefore in order to obtain the nucleotide sequence information, an intermediate amplification step is used, such as polymerase chain reaction (PCR), in order to produce enough nucleic acid for nucleotide sequence information to be generated.

Advantageously a two-step PCR strategy may be used.

For example, a first PCR ("PCR 1") is qualitative to make seed copies using low concentrations of a number of different primers in the mixture, and a second PCR ("PCR 2") is quantitative to amplify up those seed copies using adaptor primers (sometimes called anchor primers or universal primers) (i.e. using the same primers independent of whichever V/J sequences are present) to produce enough material for NGS.

Of course the skilled reader will realise that it is likely that one could amplify directly from the source material in a single PCR. Therefore a two-step PCR strategy is not essential, but is advantageous. In practice it is advantageous to perform a second "nested" PCR step which has the benefit of increasing the yield and/or detection e.g. of the clonal population.

Multiplex PCR

Suitably as an initial step once the DNA is prepared, it is subjected to a multiplex PCR. This may contain a number of primers from the V region, and/or a number of primers from the D region, and/or a number of primers from the J region—most suitably a number of primers from each of the V and the D and the J regions. Thus, these primers anneal at their individual sites throughout the nucleotide sequence being interrogated and the amplification products can be analysed after the PCR reaction to ensure integrity/reliability and proceed to sequencing. Suitably the multiplex PCR products are used in an NGS sequencing approach such that essentially the whole repertoire of PCR products is sequenced. At this point, standard data analysis techniques are used in order to determine clonality and/or pick the clone which is clearly over represented (i.e. represents the clone of interest/the tumour of interest). This determination of clonality may be carried out by any suitable technique known in the art, most suitably carried out by following the IFU for the LymphoTrack Dx TRB assay—MiSeq kit, most suitably IFU (instructions for use) 280410, which is hereby incorporated herein by reference.

Alternative Methods to Determine T Cell Clonality

Known TCR based clonality assays have employed the restriction enzyme digestion of DNA, followed by gel electrophoresis and Southern blotting using probes for the known TCR gene. Although effective and useful in practising the invention, this technique can be labour intensive, can take days to complete, can require high quantities of intact DNA to be run and can be of low sensitivity.

Thus, it may be advantageous to use PCR-based techniques to determine clonality. PCR-based techniques are routinely used for clonality assessment. Internationally accepted PCR primer sets have been introduced to further standardise PCR-based T cell clonality assays. The primers most frequently used in PCR-based TCR clonality analysis, are termed the BIOMED primer set (van Dongen et al 2003). van Dongen et al 2003 (Leukaemia 2003 volume 17 pages 2257-2317) discloses certain PCR methods that may be used in the present disclosure. In more detail, van Dongen et al 2003 discloses sets of standard primers for clonality determination, in particular reference is made to FIG. 4b, FIG. 5a, FIG. 6b, FIG. 7b, FIG. 8b, FIG. 10b, FIG. 11a, FIG. 12a and FIG. 13a of van Dongen 2003. Thus van Dongen et al 2003 is specifically incorporated by reference solely for the teaching of such PCR methods and PCR primers, and no other purpose.

Assays based on these BIOMED (van Dongen 2003) primers allow the PCR products of Ig/TCR genes to be analysed for clonality by heteroduplex analysis or GeneScanning. Amplification and sequencing of the PCR product(s) from such assays can be used to identify the J region and thus allow inference of the C region as described herein. However, it will be noted that such assays can include artefact(s) from infiltrating T cells and a rearranged TCR sequence may not be observed in a background of non-clonal T cells within a biopsy. In this situation it is desirable to sequence the products by NGS. Using NGS techniques as in the preferred embodiments described herein is advantageous for this reason.

Alternatively clonality may be determined by using the Immunoseq TCRB Assay (Adaptive Biotechnologies, 1551 Eastlake Ave E, Ste 200, Seattle, WA 98102, USA).
Primers Standard primers may be used, such as for example those provided in the LymphoTrack® Dx TRB Assay Kit—MiSeq (Invivoscribe, e.g. 10222 Barnes Canyon Road, Building 1, San Diego, CA 92121, USA).

Standard primers may be used, such as for example those provided in the BIOMED primer set (van Dongen et al 2003—see above).
ReadOut Notwithstanding the possible approaches mentioned above, or any other method of reading out the nucleic acid sequence known to the person skilled in the art, most suitably the nucleotide sequence information is read out (determined) by subjecting the nucleic acid(s), such as PCR amplified nucleic acid(s), to next generation sequencing (NGS). This is advantageous because it provides quantitative information, allowing the dominant clone in the NGS data to be easily identified. Moreover, this represents a single step—the PCR amplified nucleic acids can be directly NGS sequenced in a "one-step" procedure. Alternate methods such as probe or primer based approaches noted above, whilst effective, do not have the advantage of combination with NGS sequencing since they would require more time consuming and/or costly steps to be carried out. Thus, most suitably the sequence information is read out by NGS.

Most suitably the nucleotide sequence information is read out (determined) by using the LymphoTrack Dx TRB Assay—MiSeq assay (Invivoscribe, e.g. 10222 Barnes Canyon Road, Building 1, San Diego, CA 92121, USA).

The invention may be applied to the monitoring of minimal residual disease, because this delivers the advantage of obtaining quantitative information. For example, in applying the invention to monitoring of minimal residual disease, the percentage of the clone of interest (i.e. the T-cell cancer cells) is obtained from the NGS data whereas merely detecting the presence or absence of the characteristic transcript of that particular patient's disease (e.g. using primers to their CDR/variable regions) would only give a binary (yes/no) answer to the question or whether or not MRD is present. By using the invention to detect or monitor MRD, the quantitative information provided by the combination with NGS read out is valuable and therefore advantageous.

It is a key part of the invention that the link from the J region to the C region is exploited i.e. inferring the identity of the C region from determining the identity of the J region.
J Region Typing As will be apparent from the above, the particular reagents/techniques used to obtain the sequence information from the J-region of interest are not critical to the invention. Using NGS to obtain the information offers advantages as discussed.

However it may be that information from one or more existing NGS based clonality determination method(s) may be used to infer the C-region usage rather than requiring that a specific NGS method as disclosed herein be used to carry out the sequencing.

For example a skilled person could use a kit that allows the determination of clonality and use that information to type the J-region. This information on the J-region type can then be used with the C-region correlation which we demonstrate herein to infer the TCR Beta constant region usage as described.

Thus the skilled reader can appreciate that the invention should not be unduly restricted to the particular primer set(s) and/or design parameters exemplified herein, although those offer certain advantages. Rather, the skilled worker may use 'off the shelf' or commercially available kits or services for sequence determination (e.g. clonality determination, more commonly referred to as 'immunosequencing').

In brief, immunosequencing refers to sequence determination of the immune repertoire in a population of T-cells or B-cells. In the case of this invention, the cells of interest are T-cells. In overview, the process involves a first PCR amplification focussing on a nucleic acid segment of interest, for example a key CDR of the TCR. This is typically followed by a second amplification using different primers, which primers are conveniently tagged to facilitate sequence determination. After this second amplification, the nucleic acid products are then sequenced, most typically using NGS (next generation sequencing) techniques which exploit massively parallel determination of millions of individual sequences originating from the same original sample. This sequence data is then captured and computationally analysed to answer the questions of interest. In the context of the present invention, the output from the immunosequencing would be used to examine the sequence of the J-region, thereby allowing the particular J gene present in each sequence to be determined. Therefore, although any commercially available immunosequencing (clonality testing) kit or service may be used in the present invention, it is vital that any such kit or service provides sequence information for the J-region.

For example, kits that may be used to obtain the required data are: LymphoTrack® Dx TRB Assay Kit—MiSeq (Invivoscribe, e.g. Invivoscribe SARL, ZI Athélia IV—Le Forum—Bât B, 515 Avenue de la Tramontane, 13600 La Ciotat, France) and/or the Immunoseq TCRB Assay (Adaptive Biotechnologies, 1551 Eastlake Ave E, Ste 200, Seattle, WA 98102, USA). More suitably, kits that may be used to obtain the required data are: LymphoTrack® Dx TRB Assay Kit—MiSeq (Invivoscribe, e.g. 10222 Barnes Canyon Road, Building 1, San Diego, CA 92121, USA) and/or the clonoSEQ Assay or the Immunoseq TCRB Assay (Adaptive Biotechnologies, 1551 Eastlake Ave E, Ste 200, Seattle, WA 98102, USA).

With reference to the adaptive biotechnologies kit/service (see above), this is focussed on the CDR3 region which serves as a "unique" ID or tag for each of the individual clones within the sample. In this kit, the forward primer for the initial PCR reaction is located in the V-region, and the reverse primer for the initial amplification is located in the J-region. Thus, appropriate segments of the J-region are analysed in this manner and so the kit is suitable for use in the present invention. In the context of the invention, the sequence information of the J-region of the individual clones can be taken from the output of the kit/service, and from this information the J gene type expressed in the cell may be determined, and from that J gene type the TRBC gene type expressed in that clone may be inferred according to the present invention.

Suitably the nucleic acid extraction protocol (if any) is as in the manufacturer's instructions.

Nucleic Acid Sequencing

Of course the skilled worker could implement their own sequencing protocol to determine the nucleotide sequence information required i.e. to determine the nucleotide sequence of one or more characteristic segment(s) of the J-region as described herein.

In essence, such an approach requires accessing nucleotide sequence information of the J-region from the T-cell(s) of interest. This could be done using standard approaches such as amplification of a nucleic acid section encompassing the relevant segment(s) of the J-region, followed by sequence determination e.g. using a standard NGS approach.

Of course other approaches might equally be employed such as by separating amplification products by electrophoresis and sequencing dominant product(s), or even by cloning and in vitro manipulation of recombinant nucleic acid(s) of interest, or by diagnostic PCR using primers specific for particular J-type(s) if desired.

Such techniques are considered routine and capable of implementation by a person skilled in the art in view of the detailed disclosures provided herein. In case any further guidance is required, key elements are outlined below.

Primer Design

Primer design may be accomplished by the skilled person either manually or using freely available tools such as Eurofins Genomics' primer design tools (Eurofins Genomics, Anzinger Str. 7a, 85560 Ebersberg, Germany), or the Primer-BLAST service from National Center for Biotechnology Information, U.S. National Library of Medicine, 8600 Rockville Pike, Bethesda MD, 20894 USA, or the Prime+ program of the BioComp or SeqWEB suites (formerly the Accelrys GCG package/GCG Wisconsin Package), or any other suitable tool.

Alternatively, numerous commercially available primer design and production services may be used, for example from ThermoFisher (Thermo Fisher Scientific, 168 Third Avenue, Waltham, MA USA 02451), Eurofins Genomics (see above) or any other suitable service provider.

It is important to avoid PCR bias in the amplification reaction. This is important to ensure that accurate quantitative information is obtained.

PCR bias may be reduced or eliminated using standard techniques. For example, in outline this involves using a first range of primers at the same initial concentration for a first or preliminary amplification. The results of this amplification are then analysed. Typically, PCR bias is observed in that different PCR products are found at different concentrations in the resulting amplified nucleic acid mixture. Without wishing to be bound by theory, this is typically attributed to differing efficiencies or performance of the primers in the initial mixture. The PCR primer concentrations are then adjusted, lowering the concentrations of the best performing primers (i.e. those leading to the highest concentration of amplified nucleic acid) and increasing the concentration of under-performing primers (i.e. those leading to the lowest concentrations of nucleic acid in the amplified products). In this way, the effects of PCR bias can be dramatically reduced or eliminated, leading to a more even distribution of concentrations of PCR products in the final amplified nucleic acid mixture. This type of optimisation to reduce or eliminate PCR bias is a matter of routine for a person skilled in the art, and can be conducted by a "trial and error" analysis as outlined above.

In addition, or alternatively, PCR bias may be reduced or eliminated by using primers selected from the pools described below.

Nested/Anchored Primer Design

As is conventional in the art, the qualitative initial amplification may be followed by a quantitative amplification using universal primers situated in the 5' ends of the initial primers used for the qualitative amplification. Thus, the "nest" or "anchor" 5' tails may be incorporated into the primers used in the initial amplification in order to permit a secondary/universal/quantitative amplification to be subsequently carried out.

Suitable nest or anchor sequences are selected by the operator, as is well known in the art.

Exemplary nested primer (primer extensions) or anchor sequences are provided below.

Data Quality

The number of total sequencing reads obtained can influence data quality, as can the proportion of the total sequencing reads attributable to a single clone out of the total number of the reads obtained. In deciding whether or not the data can be relied upon, standard statistical techniques are applied, for example as in the instructions for use (IFU) of the LymphoTrack Dx TRB assay—MiSeq kit, most suitably IFU (instructions for use) 280410.

Determination of J Region

Suitably NGS is used to provide sequence information of the nucleic acid derived from/amplified from a sample.

This sequence information is then interrogated to decide which J region is present in the target sequence.

Although the sequence comparison can be done by any means, including by eye, typically a computer algorithm is used to compare a known sequence characteristic of a particular J region to the sequence information from the NGS analysis. A match between the query sequence (the known J region sequence) and the target sequence (the sequence from the NGS analysis of the nucleic acid from the patient sample) indicates the presence of that corresponding J region.

A summary of the J region sequences which are diagnostic or indicative of the identity of a particular J region present are as follows:

TABLE 1

| | J region sequence | Identity of J region | TRBC1 or TRBC2 gene inferred from identity of J region |
|---|---|---|---|
| SEQ ID NO: 1 | tgaacactgaagctttctttggacaaggcaccagactcacagttgtag | TRBJ1-1 | TRBC1 |
| SEQ ID NO: 2 | ctaactatggctacaccttcggttcggggaccaggttaaccgttgtag | TRBJ1-2 | TRBC1 |
| SEQ ID NO: 3 | ctctggaaacaccatattttggagagggaagttggctcactgttgtag | TRBJ1-3 | TRBC1 |
| SEQ ID NO: 4 | caactaatgaaaaactgttttttggcagtggaacccagctctctgtcttgg | TRBJ1-4 | TRBC1 |
| SEQ ID NO: 5 | tagcaatcagccccagcattttggtgatgggactcgactctccatcctag | TRBJ1-5 | TRBC1 |
| SEQ ID NO: 6 | ctcctataattcaccctccactttgggaatggaccaggctcactgtgacag | TRBJ1-6 allele 1 | TRBC1 |
| SEQ ID NO: 7 | ctcctataattcaccctccactttgggaacggaccaggctcactgtgacag | TRBJ1-6 allele 2 | TRBC1 |
| SEQ ID NO: 8 | ctcctacaatgagcagttcttcgggccagggacacggctcaccgtgctag | TRBJ2-1 | TRBC2 |
| SEQ ID NO: 9 | cgaacaccggggagctgttttttggagaaggctctaggctgaccgtactgg | TRBJ2-2 | TRBC2 |
| SEQ ID NO: 10 | ctgagaggcgctgctgggcgtctgggcggaggactcctggttctgg | TRBJ2-2P | TRBC2 |
| SEQ ID NO: 11 | agcacagatacgcagtattttggcccaggcacccggctgacagtgctcg | TRB.J2-3 | TRBC2 |
| SEQ ID NO: 12 | agccaaaaacattcagtacttcggcgccgggacccggctctcagtgctgg | TRB.J2-4 | TRBC2 |
| SEQ ID NO: 13 | accaagagacccagtacttcgggccaggcacgcggctcctggtgctcg | TRBJ2-5 | TRBC2 |
| SEQ ID NO: 14 | ctctggggccaacgtcctgactttcggggccgcagcaggctgaccgtgctgg | TRBJ2-6 | TRBC2 |
| SEQ ID NO: 15 | ctcctacgagcagtacttcgggccgggcaccggctcacggtcacag | TRBJ2-7 allele 1 | TRBC2 |
| SEQ ID NO: 16 | ctcctacgagcagtacgtcgggccgggcaccggctcacggtcacag | TRBJ2-7 allele 2 | TRBC2 |

The skilled worker may possibly shorten some of the sequences in Table 1, for example to about 30 bp, always provided that they remain diagnostic or indicative of the identity of a particular J region present.

It can be seen from the above table that there are different subtypes of J1 (for example J1-1, J1-2, J1-3 etc.). It can also be seen that similarly there are different subtypes for J2 (J2-1, J2-2, J2-2P etc.).

The term "J gene type" as used herein means identity of the J region i.e. whether the J region is J1 or J2. Thus, the process for identifying a J1 or J2 region being present in the sample is typically as follows:
Compare sequence data from J region of interest (i.e. from the cell/sample of interest) to reference J region sequences.
Determine J gene type (i.e. J1 or J2 gene) present in the cell/sample from the sequence comparison.

Examples of primers that can anneal in the J region are provided below in Table 2.

TABLE 2

Examples of J region-specific primers:

| Primer name | Primer sequence | |
|---|---|---|
| TRBJ1-1-Rev | 5' ctacaactgtgagtctggtgccttg 3' | SEQ ID NO: 17 |
| TRBJ1-2-Rev | 5' ctacaacggttaacctgg 3' | SEQ ID NO: 18 |
| TRBJ1-3-Rev | 5' ctacaacagtgagccaac 3' | SEQ ID NO: 19 |
| TRBJ1-4-Rev | 5' ccaagacagagagctgggttccac 3' | SEQ ID NO: 20 |
| TRBJ1-5-Rev | 5' ctaggatggagagtcgag 3' | SEQ ID NO: 21 |
| TRBJ1-6-Rev | 5' ctgtcacagtgagcctggtcccrtt 3' | SEQ ID NO: 22 |
| TRBJ2-1-Rev | 5' ctagcacggtgagccgtgt 3' | SEQ ID NO: 23 |
| TRBJ2-2-Rev | 5' ccagtacggtcagcctagag 3' | SEQ ID NO: 24 |
| TRBJ2-2P-Rev | 5' ccagaaccaggagtcctcc 3' | SEQ ID NO: 25 |
| TRBJ2-3-Rev | 5' cgagcactgtcagccgggtg 3' | SEQ ID NO: 26 |

TABLE 2-continued

Examples of J region-specific primers:

| Primer name | Primer sequence | |
|---|---|---|
| TRBJ2-4-Rev | 5' ccagcactgaga gccgggtcccg 3' | SEQ ID NO: 27 |
| TRBJ2-5-Rev | 5' cgagcaccagga gccgc 3' | SEQ ID NO: 28 |
| TRBJ2-6-Rev | 5' ccagcacggtca gcctgc 3' | SEQ ID NO: 29 |
| TRBJ2-7-Rev | 5' ctgtgaccgtga gcctggtgccgg3' | SEQ ID NO: 30 |

Forward primers may be designed by the skilled operator.

Once the J1 or J2 determination has been made, the final step is to infer the identity of the C region from the knowledge of the J region.

The term "C gene type" or "TRBC gene type" as used herein means identity of the C region i.e. whether the C region is C1 or C2 Thus, suitably the final step is:

If presence of a J1 gene is determined, the presence of a C1 gene is inferred; if presence of a J2 gene is determined, the presence of a C2 gene is inferred.

When comparing the characteristic J region sequences (reference sequences) to the target sequence (the nucleotide sequence from cell/sample of interest), suitably a 100% match is required.

Incomplete Recombinants

Occasionally cells will have undergone incomplete V/D chain rearrangement. In these circumstances, it may be possible to observe a D-J join (rather than a V-J join). Typically any information collected on D-J joins is disregarded in favour of V-J joins.

Clinical Considerations

It can be seen from of the exemplary data provided in this document that there is approximately 0.1115% of transcripts which may be J2-C1 or J1-C2 (0.1027% J1-C2+0.0088% J2-C1=0.1115%). It must be noted that linkage is at the transcript level. Therefore, this 0.1115% is not a risk of misdiagnosis, this is the rate at which the TCR on the cell surface might be "other" than expected due to an alternate transcript being produced at the nucleic acid level within the cell. In other words, the method of the invention robustly identifies the single rearranged TCR β gene in the cell being either TRBC1 or TRBC2 as inferred from the J region, but within that cell there may occasionally still be a very low level of alternate transcript produced. Thus, in practical terms, this means that the cell would display 99.8885% of the expected combination, but may display 0.1115% unexpected combinations due to this measure of transcriptional variation. In all practical terms this has minimal or zero effect on the patient/treatment/diagnostic use of the methods of the invention. This is in no way a 0.1115% error rate/misdiagnosis.

In more detail, it must be borne in mind that the 0.115% error rate refers to TCRs displayed on cell, and not to any kind of error rate in the sense of diagnosing the patient. Therefore, even if due to transcriptional variability of natural processes within the cell, there are occasionally TCRs produced which are (for example) J1-C2 or J2-C1, in all practical senses the overwhelming majority of T cells in that patient will still display accurately the particular J/C combination determined by the methods of the invention. Therefore, treatment based on the information provided by the methods of the invention will still be effective and it is an advantage of the invention that any natural variability in the transcripts produced in individual cells does not negatively affect the diagnostic value of the invention.

The inventors assert that the method is at least 99% accurate in the sense of observing 'unexpected' combinations (such as J1-C2 or J2-C1) in less than 1% of cases. In other words, the inventors assert that at least 99% of cases reflect the remarkable and surprisingly close linkage of the J and C genes upon which the invention is based.

Further Embodiments

In one aspect, the invention relates to a method comprising
 (a) determining the J gene type expressed in a cell, and
 (b) inferring from (a) the T cell receptor β chain (TRBC) gene type expressed in said cell.

In one aspect, the invention relates to a method as described above wherein step (a) comprises:
 (ai) determining the nucleotide sequence of at least a segment of said J gene from said cell; and
 (aii) comparing the nucleotide sequence determined in (ai) to one or more J gene reference nucleotide sequence(s), and
 (aiii) identifying the J gene type from sequence identity of the nucleotide sequence of the segment of said J gene of (ai) to the J gene reference nucleotide sequence(s) of (aii).

Further Advantages

Prior art methods such as IHC can require use of frozen tissue (e.g. for analysis of JOVI-1), which is labour intensive, and not always available. In addition, the qualitative nature of IHC methods may lead to misdiagnosis and/or may be prone to interpretation errors made by the diagnosing pathologist. Thus, IHC can be subjective and/or prone to operator error, which are problems in the art. It is an advantage of the invention that operator error is diminished in genomic assays since extraction protocols and sequencing are routine and may be automated.

A further advantage of the invention is that a molecular diagnosis enables the tracking of minimal residual disease (MRD) in blood with high accuracy once the clone responsible for the disease has been identified.

Patent application WO2016/051205 described an RNAscope method. However, the RNAscope assay has limitations in that the probes detect RNA, which is required to be of a sufficient length and integrity to enable probe binding. While RNAscope should enable the detection of material from fixed tissue, genomic assessment can be determined from DNA and thus provides a more stable source material for the assay, which is an advantage of the invention. Moreover, a recent publication has indicated that there is a third transcript (known as TRBCX—see Lethe et al 2017 (Immunity, Inflammation and Disease 2017; 5 (3): 346-354)). This would make it impossible to differentiate between TRBC1/2 RNA transcripts through probe design, as such RNAscope would likely not be suitable as an assay for this application, which problem is advantageously solved by the present invention.

It is a further advantage of the invention that a greater level of accuracy is provided compared to prior art methods e.g. qualitative assays or 'by-eye' methods such as IHC.

It is an advantage of the invention that the prior art practitioners have not associated the V/D chain junction (i.e. J-region) with particular C region identities. This valuable insight, including the very surprising close linkage between the J type and the C type within the TRBC gene, is a remarkable advance upon which the invention is based.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

FIG. 4 shows IMGT output.
FIG. 5A-B shows VDJ rearrangement as analyzed by IMGT.

The invention is now described by way of example which is intended to illustrate, rather than limit, embodiments of the invention as set out in the claims.

EXAMPLES

Example 1: Correlation of Joining and Constant Regions

Figure 2:
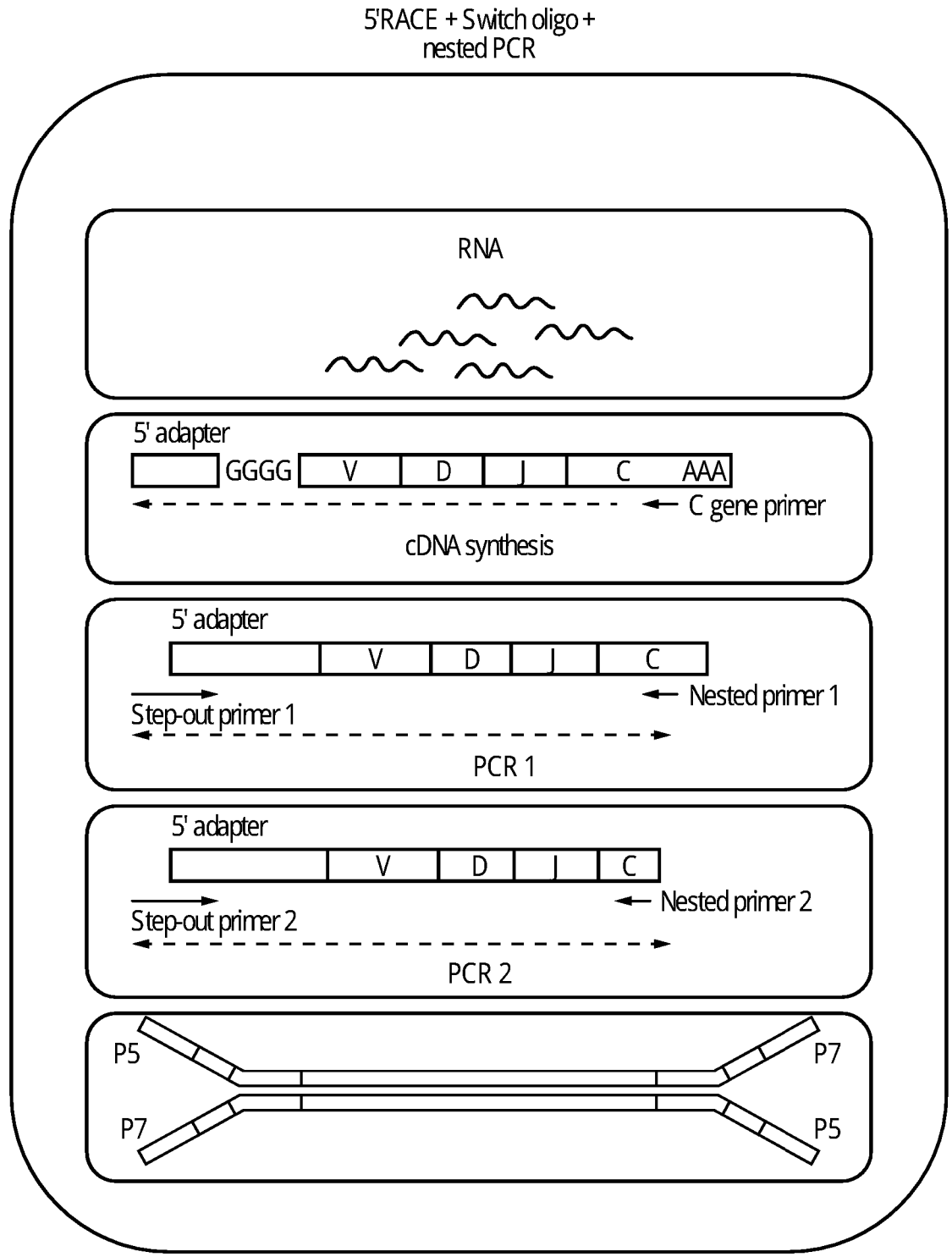
FIG. 2 shows a diagram.

TRBC transcripts were amplified using 5'RACE from 4 normal Human Tonsil samples. See FIG. 2 which shows NGS analysis of $4 \times 10^6$ unique T cell transcripts.

PCR products of ~530-620 bp in length were pooled and sequenced using Miseq illumina sequencing. Pair-end reads of 2×300 bp were acquired.

Figure 1:
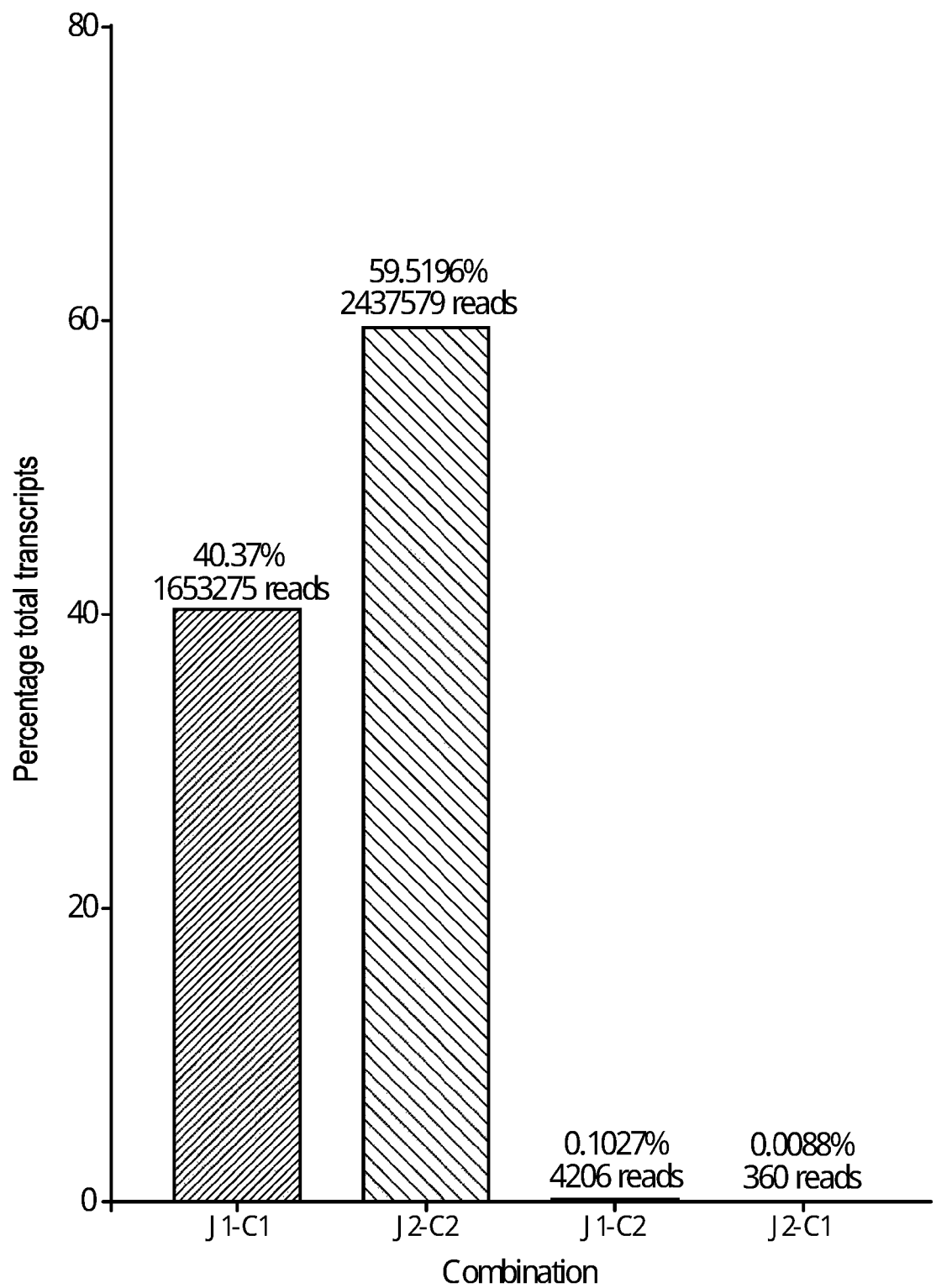
FIG. 1 shows a bar chart.

Results are shown in FIG. 1.

Example 2: Application to DNA

Figure 3:
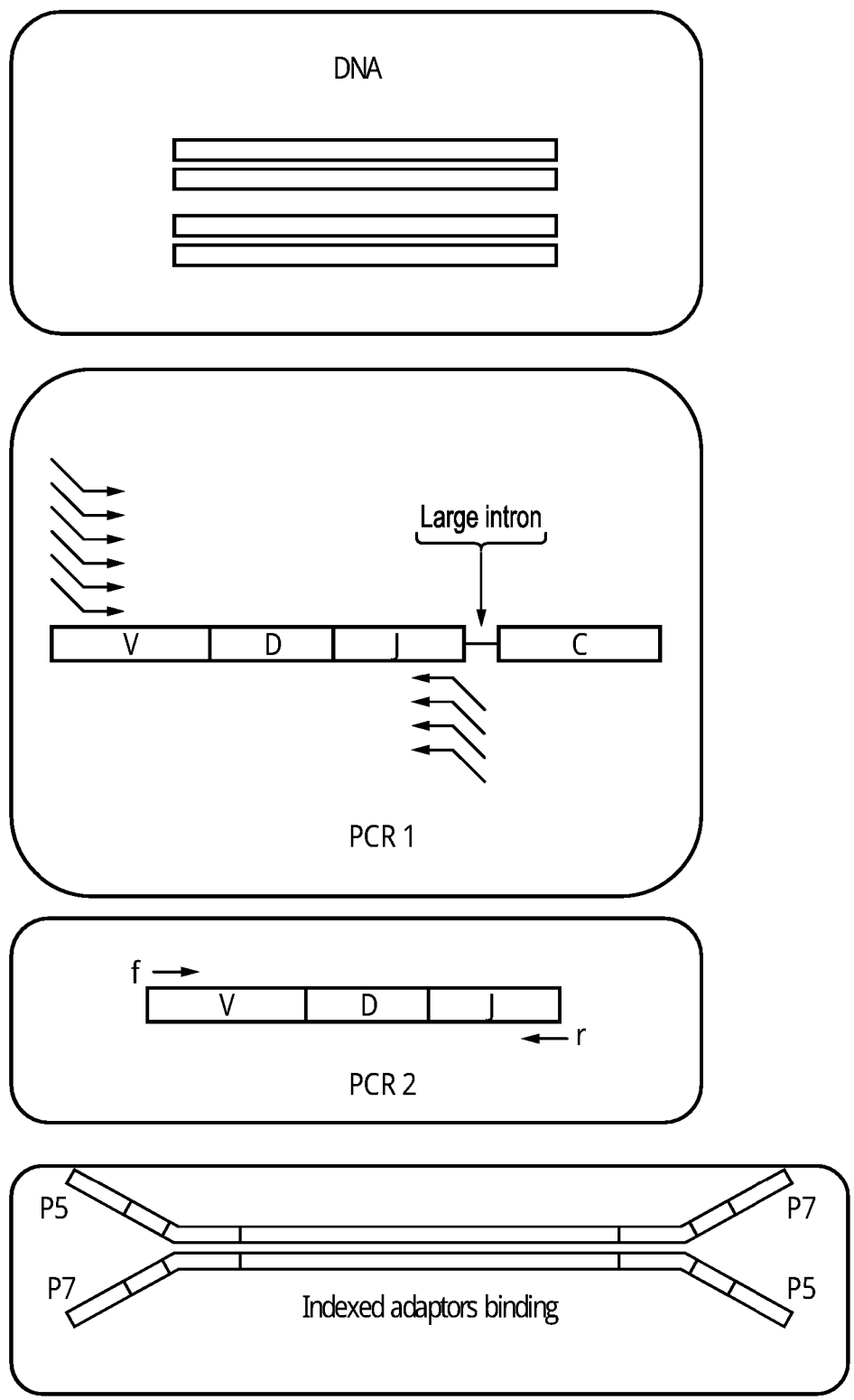
FIG. 3 shows a diagram.

We refer to FIG. 3.
Suitably the DNA is genomic DNA.

Example 3: Read Out of Sequence

We refer to FIG. 4.
IMGT output is shown.

Example 4

In this study various TRBC1/2 expressing cell lines were tested (Table 4).

Data from various T-cell lymphoma samples are also presented (Table 5).

We also provide an exemplary nucleic acid extraction protocol and exemplary NGS protocol.

In this example, data are obtained using the LymphoTrack® Dx TRB assay from Invivoscribe.

Methods

Formalin Fixed paraffin embedded (FFPE) cell lines (Jurkat, MJ, H9, HPB and Raji) and FFPE T-cell lymphoma samples were analyzed with the LymphoTrack Dx TRB Assay—MiSeq assay. DNA from each cell line and T-cell lymphoma sample was extracted from 10-15 5 μM FFPE sections using the Qiagen GeneRead DNA FFPE kit following the instructions from manufacturer unless otherwise mentioned herein.

DNA concentration was quantified using Qubit 3.0. DNA was tested in singles by the LymphoTrack Dx TRB Assay—MiSeq following the Assay IFU (280410). The FASTQ files from MiSeq runs were analyzed by the LymphoTrack Dx Software—MiSeq v2.4.3 following Software IFU (280344).

Sectioning of FFPE Tissue Blocks

1. Chill paraffin-embedded tissue blocks on ice before sectioning. Cold wax allows thinner sections to be obtained by providing support for harder elements within the tissue specimen. The small amount of moisture that penetrates the block from the melting ice will also make the tissue easier to cut.
2. Fill a waterbath with ultrapure water and heat to 40-45° C.
3. Place the blade in the holder, ensure it is secure and set the clearance angle. The clearance angle prevents contact between the knife facet and the face of the block. Follow the microtome manufacturer's instructions for guidance on setting the clearance angle. For Leica blades this is normally between 1° and 5° (FIG. 1).
4. Insert the paraffin block and orientate so the blade will cut straight across the block.
5. Carefully, approach the block with the blade and cut a few thin sections to ensure the positioning is correct. Adjust if necessary.
6. Trim the block to expose the tissue surface to a level where a representative section can be cut. Trimming is normally done at a thickness of 10-30 μm.
7. Cut sections at a thickness of about 4-5 μm (you will probably need to discard the first few sections as they are likely to contain holes caused by trimming).
8. Using tweezers, pick up the ribbons of sections and transfer to an autoclaved or DNAse free microtube (1.5 mL).
9. Proceed with DNA isolation using the Qiagen GeneRead DNA FFPE kit following the instructions from the manufacturer.

Nucleic Acid Extraction Procedure

There are several DNA extraction kits that can be used. In this example, DNA is extracted using the Qiagen's GeneRead DNA FFPE Kit.

The GeneRead DNA FFPE procedure removes paraffin and reverses formalin cross-links from the DNA sample before it is bound to the QIAamp MinElute column. After heating to remove cross-links, the DNA is accessible for the specific removal of deaminated cytosine residues by the enzyme Uracil-N-Glycosilase (UNG). The optimized reaction mixture provides conditions in which the UNG can specifically remove artificially induced uracils from the DNA obtained from the FFPE sample. After the binding of DNA to the spin column, residual contaminants such as salts are washed away by Buffers AW1 and AW2, and ethanol. Any residual ethanol, which may interfere with subsequent enzymatic reactions, is removed by an additional centrifugation step. DNA is eluted and is now ready to use in next-generation sequencing workflows.

Sequence Determination Procedure

In this example sequence is determined using the NGS protocol—LymphoTrack Dx TRB Assay—MiSeq assay:

1. Using gloved hands, remove the Master Mixes from the freezer. Allow the tubes to thaw; gently vortex to mix.
2. In a containment hood or dead air box, pipette 45 ul of Master Mix into individual wells of a PCR plate. One well for each of the Master Mixes and one Master Mix per sample, positive, negative or no template controls.
3. Add 0.2 ul EagleTaq DNA polymerase (EagleTaq @5 U/uL) to each of the Master Mixes.

4. Add 5 ul of sample DNA (at a minimum concentration of 10 ng/uL) and 5 uL of control samples to wells containing the respective Master Mix reactions and pipette up and down 5-10 times to mix.
5. Add 5 uL of molecular biology grade water to the well containing the respective Master Mix for no template control and pipette up and down 5-10 times to mix.
6. Amplify target DNA using the following thermal cycler program:

| Step | Temperature | Time | Cycle |
| --- | --- | --- | --- |
| 1 | 95° C. | 7 minutes | 1 |
| 2 | 95° C. | 45 seconds | 29X |
| 3 | 60° C. | 45 seconds | |
| 4 | 72° C. | 90 seconds | |
| 5 | 72° C. | 10 minutes | 1 |
| 6 | 15° C. | *forever* | 1 |

7. Remove the amplification plate from the thermal cycler
8. Purify the PCR products using the Agencourt AMPure XP PCR Purification system. Add 35 ul of particles to each 50 ul reaction; elute DNA in 25 ul eluate.
9. Quantify amplicons using the KAPA library quantification kit according to the kit instructions. Dilute amplicons 1:4,000 before proceeding to qPCR.
10. Pool equal amounts of amplicons from samples (do not include the no template control), dilute 1:1,000 and quantify the library using the KAPA library quantification kit.
11. Denature and dilute the library to 12 pM for MiSeq reagent kit v2 and 12-20 pM for MiSeq e=reagent kit v3 (MCS v2.6).
12. Load 600 ul of denatured and diluted library to the MiSeq Reagent Cartridge.
13. Set up a MiSeq sample sheet using the Illumina Experiment Manager (v1.4 through v1.13).
14. Start the MiSeq run.
15. Analyze and visualize the acquired data using the associated LymphoTrack Dx Software—MiSeq package.

LymphoTrack Dx Software—MiSeq Package Interpretation and Reporting

The Merged Read Summary report should be used to identify the top merged read sequences and their frequencies prior to clonality determination using the criteria listed in Table 3.

TABLE 3

| Criterion 1 | Criterion 2 | Criterion 3 | Criterion 4 | Call |
| --- | --- | --- | --- | --- |
| The total number of reads for each sample is ≥20,000. | The top merged sequence has ≥2.5% of the total reads. | There is at least one D-J rearrangement detected in the four most frequent merged sequences | The % reads for a suspected clonal merged sequence is >2X the % reads for the 5th most frequent merged sequence.[1] | EVIDENCE OF CLONALITY DETECTED |
| | | | The % reads for a suspected clonal merged sequence is ≤2X the % reads for the 5th most frequent merged sequence.[1] | No evidence of clonality detected |
| | | There are no D-J rearrangement detected in the four most frequent merged sequences | The % reads for a suspected clonal merged sequence is >2X the % reads for the 3rd most frequent merged sequence.[1] | EVIDENCE OF CLONALITY DETECTED |
| | | | The % reads for a suspected clonal merged sequence is ≤2X the % reads for the 3rd most frequent merged sequence.[1] | No evidence of clonality detected |
| The total number of reads for each sample | The top merged sequence has ≥5.0% | There is at least one D-J rearrangement detected in the | The % reads for a suspected clonal merged | EVIDENCE OF CLONALITY DETECTED |

TABLE 3-continued

| Criterion 1 | Criterion 2 | Criterion 3 | Criterion 4 | Call |
|---|---|---|---|---|
| is ≥10,000 and <20,000. | of the total reads. | four most frequent merged sequences | sequence is >2X the % reads for the 5th most frequent merged sequence.[1] | |
| | | | The % reads for a suspected clonal merged sequence is ≤2X the % reads for the 5th most frequent merged sequence.[1] | No evidence of clonality detected |
| | | There are no D-J rearrangement detected in the four most frequent merged sequences | The % reads for a suspected clonal merged sequence is >2X the % reads for the 3rd most frequent merged sequence.[1] | EVIDENCE OF CLONALITY DETECTED |
| | | | The % reads for a suspected clonal merged sequence is ≤2X the % reads for the 3rd most frequent merged sequence.[1] | No evidence of clonality detected |
| The total number of reads for each sample is <10,000. | N/A | N/A | N/A | Not evaluable |

[1]Software calculations are rounded to the nearest tenth for comparison.

Results

Diagnostic and histology data for the T cell lymphoma samples can be found in Table 6.

Referring to the tables below, "total count" means the total number of reads obtained from the NGS instrument. "Length" means the length of read obtained. "V-gene" refers to the V gene type detected. "J-gene" refers to the J gene type detected. "Percentage total reads" is the percentage out of the total number of reads which matched this specific gene sequence as determined.

It will be observed that certain rows in the table(s) show more than one V gene or J gene type from a single sample—this can happen when a D-J join is detected as well as a V-J join. As explained elsewhere in this document, any D-J joins detected are discarded since they represent incomplete recombination events. Suitably the J type determined is from a V-J joined J gene (J region).

Cell Lines

DNA concentrations, amplicon concentrations and Top 1 and/or 2 clonal rearrangements for the cell lines are summarized in Table 4:

TABLE 4

Top 1 and/or 2 clonal rearrangements for the cell lines

| Cell Type | DNA input into PCR (ng) | Total Count | Length | V-gene | J-gene | % total reads | TRBC (C1 or C2) |
|---|---|---|---|---|---|---|---|
| Jurkat | 30 | 658,707 | 198 | Vb12-4 | Jb1-2 | 75.92 | C1 |
| HPB-ALL | 25 | 33,238 | 219 | Vb5-5 | Jb2-5 | 1.43 | C2 |
| H9 | 50 | 588,668 | 205 | Vb13 | Jb1-2 | 89.18 | C1 |
| MJ | 6.5 | 92,995 | 219 | Db1 | Jb1-1 | 19.69 | C1 |
| | | | 189 | Vb28 | Jb1-1 | 17.55 | |
| Raji | 25 | 46,883 | 201 | Db2 | Jb2-2 | 0.08 | Non-clonal |

Shading Represents Incomplete D-J Rearrangements

One cell line sample (MJ) was detected with 2 clonal rearrangements. The D/J rearrangements are an incomplete rearrangement and will spliced out in V-J-C combination. Data from incomplete rearrangement(s) such as D/J rearrangements is suitably discarded. Focus is on the complete V/J rearrangements. Thus for 'MJ', the 'Db1' row of data is discarded due to being incomplete rearrangement. The Vb28 row of data is retained.

One cell line sample (Raji) was detected with the top % total reads less than 1.0% and is non-clonal. Data which is non-clonal is suitably discarded. Focus is on data which is clonal.

Following discarded data as explained above, Table 4A is produced.

TABLE 4A

Top 1 and/or 2 clonal rearrangements for the cell lines

| Cell Type | DNA input into PCR (ng) | Total Count | Length | V-gene | J-gene | % total reads | TRBC (C1 or C2) |
|---|---|---|---|---|---|---|---|
| Jurkat | 30 | 658,707 | 198 | Vb12-4 | Jb1-2 | 75.92 | C1 |
| HPB-ALL | 25 | 33,238 | 219 | Vb5-5 | Jb2-5 | 1.43 | C2 |
| H9 | 50 | 588,668 | 205 | Vb13 | Jb1-2 | 89.18 | C1 |
| MJ | 6.5 | 92,995 | 189 | Vb28 | Jb1-1 | 17.55 | C1 |

Based on J1-C1 and J2-C2 correlations, MJ is C1.

Three cell line samples (Jurkat, HPB-ALL and H9) were detected with one V-J rearrangement. Based on J1-C1 and J2-C2 correlation, Jurkat and H9 cells are C1 and HPB-ALL cells are C2.

All cell line data is consistent with the reported literature.

Samples

DNA concentrations, amplicon concentrations and Top 1 and/or 2 clonal rearrangements for the T-cell lymphoma samples are summarized in Table 5.

Four T-cell lymphoma samples (F19542.1a, F19539.1c, F19538.A1b and TS18-1512A) are detected with 2 clonal rearrangements. Data from incomplete rearrangement(s) such as D/J rearrangements is suitably discarded. Focus is on the complete V/J rearrangements. Thus for these samples the 'Db1' or 'Db2' rows of data are discarded due to being incomplete rearrangements. The Vb13, Vb29-1, Vb12-4 and Vb6-4 rows of data are retained.

Two samples (TS18-1508A and TS18-1499A) are detected with either none-J or D-J rearrangements, and/or the top % total reads less than 1.0% and are considered non-clonal. Data from remaining samples determined to be non-clonal or not-evaluable according to IFU 280410 of the LymphoTrack kit, more suitably according to Table 3 above, are discarded. Data which is non-clonal is suitably discarded. Focus is on data which is clonal.

Following discarded data as explained above, Table 5A is produced.

TABLE 5

Top 1 and/or 2 clonal rearrangements for the T cell lymphoma samples
10 T-cell Lymphoma FFPE Samples: Diluted to 10 ng/μL

| Sample ID | DNA Conc. (ng/μL) | DNA input (ng) | Amplicon Conc. (nM) | Total count | Length | V-gene | J-gene | % total reads | Clonality | TCR Call based on J1 or J2 (C1 or C2) |
|---|---|---|---|---|---|---|---|---|---|---|
| F19542.1a | 28.9 | 50 | 1.5 | 27,344 | 215 | Vb13 | Jb1-4 | 8.64 | Clonal | C1 |
|  |  |  |  |  | 208 | Db1 | Jb1-2 | 5.18 |  |  |
| F19539.1C | 52.0 | 50 | 5.1 | 34,498 | 216 | Vb29-1 | Jb2-2 | 5.38 | Clonal | C2 |
|  |  |  |  |  | 214 | Db1 | Jb1-1 | 4.26 |  |  |
| F45038.b | 58.0 | 50 | 14.0 | 104,194 | 186 | Vb12-4 | Jb1-6 | 38.00 | Clonal | C1 |
| F19538.A1b | 42.4 | 50 | 7.1 | 42,097 | 198 | Vb12-4 | Jb1-6 | 14.32 | Clonal | C1 |
|  |  |  |  |  | 196 | Db2 | Jb2-7 | 6.51 |  |  |
| FF6679.B1b | 45.8 | 50 | 7.2 | 70,579 | 146 | VB14 | Jb2-7 | 0.48 | Non-Clonal | [b]C1, C2 Neg |
| F45029.B5 | 0.58 | 2.9 | N/A | N/A | N/A | N/A | N/A | N/A | [c]Not evaluable | [c]Not evaluable |
| TS18-1508A | 29.9 | 50 | 1.5 | 18,347 | 60 | none | Jb1-1 | 0.38 | Non-Clonal | [a]C1, C2 Neg |
| TS18-1513A | 51.0 | 50 | 2.8 | 79,716 | 214 | Db1 | Jb2-7 | 1.11 | Non-Clonal | [b]C1, C2 Neg |

TABLE 5-continued

Top 1 and/or 2 clonal rearrangements for the T cell lymphoma samples
10 T-cell Lymphoma FFPE Samples: Diluted to 10 ng/μL

| Sample ID | DNA Conc. (ng/μL) | DNA input (ng) | Amplicon Conc. (nM) | Total count | Length | V-gene | J-gene | % total reads | Clonality | TCR Call based on J1 or J2 (C1 or C2) |
|---|---|---|---|---|---|---|---|---|---|---|
| TS18-1512A | 53.0 | 50 | 5.8 | 69,034 | 192 | Vb6-4 | Jb2-3 | 23.09 | Clonal | C2 |
|  |  |  |  |  | 205 | Db1 | Jb1-6 | 18.00 |  |  |
| TS18-1499A | 36.1 | 50 | 2.8 | 20,549 | 189 | Db2 | Jb2-7 | 3.32 | Non-Clonal | [b]C1, C2 Neg |

[a]The top % total reads is less than the clonal cutoff 5.0% for samples with the total reads ≥10,000 reads and <20,000. According to IFU 280410 and/or Table 3, this sample is called "Non-clonal".
[b]The top % total reads is less than the clonal cutoff 2.5% for samples with the total reads ≥20,000 reads. According to IFU 280410 and/or Table 3, this sample is called "Non-clonal".
[c]The minimum DNA input requirement is 50 ng per sample. According to IFU 280410, this sample is considered as "Not evaluable". Shading represents incomplete D-J rearrangements

TABLE 5A

Top 1 and/or 2 clonal rearrangements for the T cell lymphoma samples
T-cell Lymphoma FFPE Samples: Diluted to 10 ng/μL

| Sample ID | DNA Conc. (ng/μL) | DNA input (ng) | Amplicon Conc. (nM) | Total count | Length | V-gene | J-gene | % total reads | Clonality | TCR Call based on J1 or J2 (C1 or C2) |
|---|---|---|---|---|---|---|---|---|---|---|
| F19542.1a | 28.9 | 50 | 1.5 | 27,344 | 215 | Vb13 | Jb1-4 | 8.64 | Clonal | C1 |
| F19539.1C | 52.0 | 50 | 5.1 | 34,498 | 216 | Vb29-1 | Jb2-2 | 5.38 | Clonal | C2 |
| F45038.b | 58.0 | 50 | 14.0 | 104,194 | 186 | Vb12-4 | Jb1-6 | 38.00 | Clonal | C1 |
| F19538.A1b | 42.4 | 50 | 7.1 | 42,097 | 198 | Vb12-4 | Jb1-6 | 14.32 | Clonal | C1 |
| F45029.B5 | 0.58 | 2.9 | N/A | N/A | N/A | N/A | N/A | N/A | [c]Not evaluable | [c]Not evaluable |
| TS18-1512A | 53.0 | 50 | 5.8 | 69,034 | 192 | Vb6-4 | Jb2-3 | 23.09 | Clonal | C2 |

TABLE 6

Diagnostic and histology data for the T cell lymphoma samples

| Sample ID | Histological Tumor Type | Tissue Type | [a]TCR IHC |
|---|---|---|---|
| F19542.1a | Peripheral T cell lymphoma, nos | Lymph Node, Axillary | + |
| F19539.1c | Peripheral T cell lymphoma, nos | Lymph Node | + |
| F45038.b | Peripheral T cell lymphoma, nos | Lymph Node | + |
| F19538.A1b | Angioimmunoblastic T cell lymphoma | Lymph Node, Inguinal | + |
| FF6679.B1b | Hodgkin's like, Anaplastic Large T-cell (Ki-1+) lymphoma | Lymph Node, Mediastinal | + |
| F45029.B5 | Peripheral T cell lymphoma, nos | Lymph Node | + |
| TS18-1508A | Cutaneous, Anaplastic Large T-cell lymphoma, ALK-positive | Lymph Node | − |
| TS18-1513A | Anaplastic Large T-cell lymphoma, ALK-positive | Lymph Node, Cervical | + |
| TS18-1512A | Cutaneous, Anaplastic Large T-cell lymphoma, ALK-positive | Lymph Node, Axillary | + |
| TS18-1499A | Anaplastic Large T-cell lymphoma, ALK-positive | Lymph Node, Cervical | − |

[a]TCR Immunohistochemistry (IHC) staining was performed to determine the presence of T cell receptors in the samples. 8/10 samples were TCR positive and 2/10 samples were TCR negative by IHC.
Based on J1-C1 and J2-C2 correlations (Table 5A), F1.9542.1a is C1, F19539.1C and TS18-1512A are C2.
One sample (F45038.b) is detected with one V-J rearrangement (Vb12-4/Jb1-6). Based on J1-C1 and J2-C2 correlation, this sample is C1.

Based on J1-C1 and J2-C2 correlations (Table 5A), F19542.1a is C1, F19539.1c and TS18-1512A are C2.

One sample (F45038.b) is detected with one V-J rearrangement (Vb12-4/Jb1-6). Based on J1-C1 and J2-C2 correlation, this sample is C1.

In summary, a sample is identified as having TRBC1 (C1) or TRBC2 (C2) positivity if the sample is determined to be clonal by the LymphoTrack Dx TRB Assay—MiSeq; where the presence of a J1 sequence determines C1 positivity or the presence of a J2 sequence determines C2 positivity.

Although illustrative embodiments of the invention have been disclosed in detail herein, with reference to the accompanying drawings, it is to be understood that the invention is not limited to the precise embodiment(s) shown and that various changes and modifications can be effected therein by

The invention claimed is:

1. A method of treating peripheral T cell lymphoma (PTCL) in a subject comprising:
   (1) determining the T cell receptor β chain constant region (TRBC) gene type of a PTCL cell from said subject is a TRBC1 type or a TRBC2 type with a method comprising:
   (a) determining the J gene type expressed in said cell by:
      (i) extracting nucleic acid of the J gene from said cell;
      (ii) sequencing at least a segment of the J gene from said nucleic acid;
      (iii) comparing the nucleotide sequence determined in (ii) to one or more J gene reference nucleotide sequence(s), wherein the reference nucleotide sequences comprise SEQ ID NOs: 1-16; and
      (iv) identifying the J gene type from sequence identity of the nucleotide sequence of the segment of said J gene of (ii) to the J gene reference nucleotide sequence(s) of (iii), and
   (b) inferring from (a) the TRBC gene type expressed in said cell,
      wherein the TRBC gene in the cell from the subject is determined to be a TRBC1 gene when the J gene sequence is determined to comprise the nucleotide sequence of one of SEQ ID NO: 1-7 or the TRBC gene in the cell from the subject is determined to be a TRBC2 gene when the J gene sequence is determined to comprise the nucleotide sequence of one of SEQ ID NO: 8-16; and
   (2) administering to said subject a CAR T cell targeted to the TRBC type determined in (1).

* * * * *

SEQUENCE LISTING

<160> NUMBER OF SEQ ID NOS: 37

<210> SEQ ID NO 1
<211> LENGTH: 48
<212> TYPE: DNA
<213> ORGANISM: Homo sapiens

<400> SEQUENCE: 1
tgaacactga agctttcttt ggacaaggca ccagactcac agttgtag                 48

<210> SEQ ID NO 2
<211> LENGTH: 48
<212> TYPE: DNA
<213> ORGANISM: Homo sapiens

<400> SEQUENCE: 2
ctaactatgg ctacaccttc ggttcgggga ccaggttaac cgttgtag                 48

<210> SEQ ID NO 3
<211> LENGTH: 50
<212> TYPE: DNA
<213> ORGANISM: Homo sapiens

<400> SEQUENCE: 3
ctctggaaac accatatatt ttggagaggg aagttggctc actgttgtag               50

<210> SEQ ID NO 4
<211> LENGTH: 51
<212> TYPE: DNA
<213> ORGANISM: Homo sapiens

<400> SEQUENCE: 4
caactaatga aaaactgttt tttggcagtg gaacccagct ctctgtcttg g             51

<210> SEQ ID NO 5
<211> LENGTH: 50
<212> TYPE: DNA
<213> ORGANISM: Homo sapiens

<400> SEQUENCE: 5
tagcaatcag ccccagcatt ttggtgatgg gactcgactc tccatcctag               50

<210> SEQ ID NO 6
<211> LENGTH: 53
<212> TYPE: DNA
<213> ORGANISM: Homo sapiens

<400> SEQUENCE: 6
ctcctataat tcacccctcc actttgggaa tgggaccagg ctcactgtga cag           53

<210> SEQ ID NO 7
<211> LENGTH: 53
<212> TYPE: DNA
<213> ORGANISM: Homo sapiens

<400> SEQUENCE: 7
ctcctataat tcacccctcc actttgggaa cgggaccagg ctcactgtga cag           53

<210> SEQ ID NO 8
<211> LENGTH: 50
<212> TYPE: DNA
<213> ORGANISM: Homo sapiens

<400> SEQUENCE: 8
ctcctacaat gagcagttct tcgggccagg gacacggctc accgtgctag                 50

<210> SEQ ID NO 9
<211> LENGTH: 51
<212> TYPE: DNA
<213> ORGANISM: Homo sapiens

<400> SEQUENCE: 9
cgaacaccgg ggagctgttt tttggagaag gctctaggct gaccgtactg g               51

<210> SEQ ID NO 10
<211> LENGTH: 46
<212> TYPE: DNA
<213> ORGANISM: Homo sapiens

<400> SEQUENCE: 10
ctgagaggcg ctgctgggcg tctgggcgga ggactcctgg ttctgg                     46

<210> SEQ ID NO 11
<211> LENGTH: 49
<212> TYPE: DNA
<213> ORGANISM: Homo sapiens

<400> SEQUENCE: 11
agcacagata cgcagtattt tggcccaggc acccggctga cagtgctcg                  49

<210> SEQ ID NO 12
<211> LENGTH: 50
<212> TYPE: DNA
<213> ORGANISM: Homo sapiens

<400> SEQUENCE: 12
agccaaaaac attcagtact tcggcgccgg gacccggctc tcagtgctgg                 50

<210> SEQ ID NO 13
<211> LENGTH: 48
<212> TYPE: DNA
<213> ORGANISM: Homo sapiens

<400> SEQUENCE: 13
accaagagac ccagtacttc gggccaggca cgcggctcct ggtgctcg                   48

<210> SEQ ID NO 14
<211> LENGTH: 53
<212> TYPE: DNA
<213> ORGANISM: Homo sapiens

<400> SEQUENCE: 14
ctctggggcc aacgtcctga ctttcggggc cggcagcagg ctgaccgtgc tgg             53

<210> SEQ ID NO 15
<211> LENGTH: 47
<212> TYPE: DNA
<213> ORGANISM: Homo sapiens

<400> SEQUENCE: 15
ctcctacgag cagtacttcg ggccgggcac caggctcacg gtcacag                    47

<210> SEQ ID NO 16
<211> LENGTH: 47
<212> TYPE: DNA
<213> ORGANISM: Homo sapiens

<400> SEQUENCE: 16
ctcctacgag cagtacgtcg ggccgggcac caggctcacg gtcacag        47

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
ctacaactgt gagtctggtg ccttg                                25

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
ctacaacggt taacctgg                                        18

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
ctacaacagt gagccaac                                        18

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
ccaagacaga gagctgggtt ccac                                 24

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
ctaggatgga gagtcgag                                        18

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ctgtcacagt gagcctggtc ccrtt                                    25

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
ctagcacggt gagccgtgt                                           19

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ccagtacggt cagcctagag                                          20

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
ccagaaccag gagtcctcc                                           19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
cgagcactgt cagccgggtg                                          20

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
ccagcactga gagccgggtc ccg                                      23

<210> SEQ ID NO 28
<211> LENGTH: 17
<212> TYPE: DNA
<213> ORGANISM: Artificial Sequence
<220> FEATURE:
<223> OTHER INFORMATION: Primer

<400> SEQUENCE: 28
cgagcaccag gagccgc                                             17

<210> SEQ ID NO 29
<211> LENGTH: 18

<212> TYPE: DNA
<213> ORGANISM: Artificial Sequence
<220> FEATURE:
<223> OTHER INFORMATION: Primer

<400> SEQUENCE: 29
ccagcacggt cagcctgc                                                 18

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
ctgtgaccgt gagcctggtg cccgg                                         25

<210> SEQ ID NO 31
<211> LENGTH: 548
<212> TYPE: DNA
<213> ORGANISM: Artificial Sequence
<220> FEATURE:
<223> OTHER INFORMATION: 38675309_B97#1_TRBC2 reference sequence for a
      re-arranged beta chain

<400> SEQUENCE: 31
cgacgtggat tatccatgaa cgcaaagcag tggtatcaac gcagagtacg cgggagggga      60
gaggccatca cttgaagatg ctgagtcttc tgctccttct cctgggacta ggctctgtgt     120
tcagtgctgt catctctcaa aagccaagca gggatatctg tcaacgtgga acctccctga     180
cgatccagtg tcaagtcgat agccaagtca ccatgatgtt ctggtaccgt cagcaacctg     240
gacagagcct gacactgatc gcaactgcaa atcagggctc tgaggccaca tatgagagtg     300
gatttgtcat tgacaagttt cccatcagcc gcccaaacct aacattctca actctgactg     360
tgagcaacat gagccctgaa gacagcagca tatatctctg cagcgccaaa gggaccctct     420
acgagcagta cttcgggccg ggcaccaggc tcacggtcac agaggacctg aaaaacgtgt     480
tcccacccga ggtcgctgtg tttgagccat cagaagcaga gatctcccac acccaaaagg     540
ccacactg                                                            548

<210> SEQ ID NO 32
<211> LENGTH: 290
<212> TYPE: DNA
<213> ORGANISM: Homo sapiens
<220> FEATURE:
<221> NAME/KEY: misc_feature
<222> LOCATION: (1)..(290)
<223> OTHER INFORMATION: L36092 Homsap TRBV29-1*01 F  Folch, G. and
      Lefranc, M.-P., Exp. Clin. Immunogenet., 17, 42-54 (2000))
      (L36092 - GenBank germline beta T-cell receptor locus)

<400> SEQUENCE: 32
agtgctgtca tctctcaaaa gccaagcagg gatatctgtc aacgtggaac ctccctgacg      60
atccagtgtc aagtcgatag ccaagtcacc atgatgttct ggtaccgtca gcaacctgga     120
cagagcctga cactgatcgc aactgcaaat cagggctctg aggccacata tgagagtgga     180
tttgtcattg acaagtttcc catcagccgc ccaaacctaa cattctcaac tctgactgtg     240
agcaacatga gccctgaaga cagcagcata tatctctgca gcgttgaaga               290

<210> SEQ ID NO 33
<211> LENGTH: 96

```
<212> TYPE: PRT
<213> ORGANISM: Homo sapiens
<220> FEATURE:
<221> NAME/KEY: MISC_FEATURE
<222> LOCATION: (1)..(96)
<223> OTHER INFORMATION: L36092 Homsap TRBV29-1*01 F (Folch, G. and
      Lefranc, M.-P., Exp. Clin. Immunogenet., 17, 42-54 (2000))
      (L36092 - GenBank germline beta T-cell receptor locus)

<400> SEQUENCE: 33

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Glu
                85                  90                  95

<210> SEQ ID NO 34
<211> LENGTH: 19
<212> TYPE: PRT
<213> ORGANISM: Homo sapiens

<400> SEQUENCE: 34

Ala Lys Gly Thr Leu Tyr Glu Gln Tyr Phe Gly Pro Gly Thr Arg Leu
1               5                   10                  15

Thr Val Thr

<210> SEQ ID NO 35
<211> LENGTH: 54
<212> TYPE: DNA
<213> ORGANISM: Homo sapiens

<400> SEQUENCE: 35
ccaggaccct ctacgagcag tacttcgggc cgggcaccag gctcacggtc acag        54

<210> SEQ ID NO 36
<211> LENGTH: 63
<212> TYPE: DNA
<213> ORGANISM: Homo sapiens

<400> SEQUENCE: 36
tgcagcgcca aagggaccct ctacgagcag tacttcgggc cgggcaccag gctcacggtc    60
aca                                                                  63

<210> SEQ ID NO 37
<211> LENGTH: 36
<212> TYPE: DNA
<213> ORGANISM: Homo sapiens

<400> SEQUENCE: 37
tgcagcgcca aagggaccct ctacgagcag tacttc                              36
```